(12) United States Patent
Terao et al.

(10) Patent No.: US 10,968,178 B2
(45) Date of Patent: Apr. 6, 2021

(54) IP6K INHIBITORS

(71) Applicant: TAKEDA PHARMACEUTICAL COMPANY LIMITED, Osaka (JP)

(72) Inventors: Yoshito Terao, Fujisawa (JP); Masashi Takahashi, Fujisawa (JP); Ryoma Hara, Fujisawa (JP); Kousuke Hidaka, Fujisawa (JP); Hideki Furukawa, Fujisawa (JP); Takeshi Yamasaki, Fujisawa (JP); Shizuo Kasai, Fujisawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 16/496,530

(22) PCT Filed: Mar. 29, 2018

(86) PCT No.: PCT/JP2018/014502
§ 371 (c)(1),
(2) Date: Sep. 23, 2019

(87) PCT Pub. No.: WO2018/182051
PCT Pub. Date: Oct. 4, 2018

(65) Prior Publication Data
US 2020/0377458 A1 Dec. 3, 2020

(30) Foreign Application Priority Data
Mar. 30, 2017 (JP) .............................. JP2017-066579

(51) Int. Cl.
| C07D 209/96 | (2006.01) |
| C07D 401/12 | (2006.01) |
| C07D 403/12 | (2006.01) |
| C07D 471/10 | (2006.01) |
| C07D 491/052 | (2006.01) |
| A61P 3/10 | (2006.01) |
| A61P 9/04 | (2006.01) |

(52) U.S. Cl.
CPC .............. *C07D 209/96* (2013.01); *A61P 3/10* (2018.01); *A61P 9/04* (2018.01); *C07D 401/12* (2013.01); *C07D 403/12* (2013.01); *C07D 471/10* (2013.01); *C07D 491/052* (2013.01)

(58) Field of Classification Search
None
See application file for complete search history.

(56) References Cited

U.S. PATENT DOCUMENTS

| 4,617,302 | A | 10/1986 | Robertson |
| 7,045,527 | B2 * | 5/2006 | Chen ........................ A61P 25/06 514/278 |
| 10,300,075 | B2 | 5/2019 | Brown et al. |
| 10,500,213 | B2 | 12/2019 | Brown et al. |
| 10,632,128 | B2 | 4/2020 | Harrington et al. |
| 2004/0142956 | A1 | 7/2004 | Chen et al. |
| 2007/0078152 | A1 | 4/2007 | Chen et al. |
| 2018/0282282 | A1 | 10/2018 | Chan et al. |
| 2018/0289720 | A1 | 10/2018 | Harrington et al. |
| 2019/0201412 | A1 | 7/2019 | Brown et al. |
| 2019/0381064 | A1 | 12/2019 | Harrington |
| 2020/0171043 | A1 | 6/2020 | Harrington et al. |

FOREIGN PATENT DOCUMENTS

| EP | 0 178 876 | 4/1986 |
| WO | 2004/028459 | 4/2004 |
| WO | 2018/183418 | 10/2018 |
| WO | 2018/183964 | 10/2018 |

OTHER PUBLICATIONS

Search Report dated Aug. 17, 2020 issued in corresponding Chilean Patent Application No. 201902662.
International Search Report dated Jul. 12, 2018 in International (PCT) Application No. PCT/JP2018/014502.
Barker et al., "Inositol pyrophosphates: structure, enzymology and function", Cellular and Molecular Life Sciences, vol. 66, pp. 3851-3871, 2009.
Azevedo et al., "The signaling role of inositol hexakisphosphate kinases (IP6Ks)", Advances in Enzyme Regulation, vol. 51, pp. 74-82, 2011.

(Continued)

*Primary Examiner* — Kamal A Saeed
(74) *Attorney, Agent, or Firm* — Wenderoth, Lind & Ponack, L.L.P.

(57) ABSTRACT

The present invention aims to provide a heterocyclic compound having an IP6K inhibitory action and expected to be useful as a prophylactic or therapeutic agent for—diseases such as cardiac failure, diabetes and the like. A compound represented by the formula (I): wherein each symbol is as defined in the SPECIFICATION, or a salt thereof has an IP6K inhibitory action and is expected to be useful as a prophylactic or therapeutic agent for diseases such as cardiac failure, diabetes and the like.

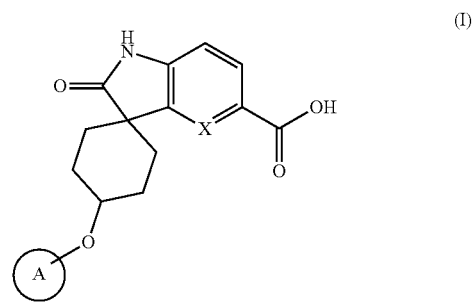

18 Claims, 10 Drawing Sheets

(56) References Cited

OTHER PUBLICATIONS

Lin et al., "Structural Analysis and Detection of Biological Inositol Pyrophosphates Reveal That the Family of VIP/Diphosphoinositol Pentakisphosphate Kinases Are 1/3-Kinases", Journal of Biological Chemistry, vol. 284, No. 3, pp. 1863-1872, 2009.

Saiardi et al., "Synthesis of diphosphoinositol pentakisphosphate by a newly identified family of higher inositol polyphosphate kinases", Current Biology, vol. 9, pp. 1323-1326, 1999.

Draškovič et al., "Inositol Hexakisphosphate Kinase Products Contain Diphosphate and Triphosphate Groups", Chemistry & Biology, vol. 15, pp. 274-286, 2008.

Choi et al., "Purification, Sequencing, and Molecular Identification of a Mammalian PP-InsP$_5$ Kinase That Is Activated When Cells Are Exposed to Hyperosmotic Stress", The Journal of Biological Chemistry, vol. 282, No. 42, pp. 30763-30775, 2007.

Fridy et al., "Cloning and Characterization of Two Human VIP1-like Inositol Hexakisphosphate and Diphosphoinositol Pentakisphosphate Kinases", The Journal of Biological Chemistry, vol. 282, No. 42, pp. 30754-30762, 2007.

Wang et al."Structural basis for an inositol pyrophosphate kinase surmounting phosphate crowding", Nature Chemical Biology, vol. 8, pp. 111-116, 2012.

Shears, "Inositol pyrophosphates: why so many phosphates?", Advances in Biological Regulation, vol. 57, pp. 203-216, 2015.

Wilson et al., "Inositol pyrophosphates: between signalling and metabolism", Biochemical Journal, vol. 452, No. 3, pp. 369-379, 2013.

Albert et al., "Biological variability mammalian cells", Biochemical Journal, in the structures of diphosphoinositol polyphosphates in *Dictyostelium discoideum* and vol. 327, pp. 553-560, 1997.

Chakraborty et al., "Inositol Pyrophosphates Inhibit Cell, vol. 143, pp. 897-910, 2010 Akt Signaling, Thereby Regulating Insulin Sensitivity and Weight Gain", Cell, vol. 143, pp. 897-910, 2010.

Rao et al., "Inositol pyrophosphates promote tumor growth and metastasis by antagonizing liver kinase B1", Proceedings of the National Academy of Sciences, vol. 112, No. 6, pp. 1773-1778, 2015.

Nagata et al., "Inositol Hexakisphosphate Kinase 2 Promotes Cell Death in Cells with Cytoplasmic TDP-43 Aggregation", Molecular Neurobiology, vol. 53, No. 8, pp. 5377-5383, 2016.

Moritoh et al., "Inositol Hexakisphosphate Kinase 3 Regulates Metabolism and Lifespan in Mice", Scientific Reports, vol. 6, No. 1, srep32072, 2016.

\* cited by examiner (ORTEP figure, 50% probability level)

IP6K INHIBITORS

TECHNICAL FIELD

The present invention relates to a heterocyclic compound having an inositol hexakisphosphate kinase (Inositol hexakisphosphate kinase) (sometimes to be abbreviated as "IP6K" in the present specification) inhibitory action and expected to be useful as a prophylactic or therapeutic agent for diseases such as cardiac failure, diabetes and the like.

BACKGROUND OF THE INVENTION

IP6K is a molecule involved in many intracellular signaling by generating inositol pyrophosphate (non-patent documents 1, 2). Inositol pyrophosphate is a low molecule with high energy and the production thereof is known to be mediated by two kinds of enzymes. The two kinds are IP6K having 5 kinase activity (non-patent documents 3-5) and diphosphoinositol pentakisphosphate kinase having 1 kinase activity (PPIP5K (non-patent documents 6-8)).

The 5 kinase activity of IP6K produces 5-PP-InsP$_4$ from myo-inositol (1,3,4,5,6)-pentakisphosphate (InsP$_5$), 5-PP-InsP$_5$ from InsP$_6$ (5-InsP$_7$ (non-patent document 9), hereinafter to be indicated as IP7), and 1,5-PP22-InsP$_4$ (InsP$_8$) from 1-PP-InsP$_5$. Among these, 127 is the most studied inositol pyrophosphate produced by IP6K and controls many biological reactions by directly binding to the target protein or through the mechanism of pyrophosphorylation (transfer of β-phosphoric acid of pyrophosphoric acid moiety of 127 to phosphorylated serine residue of target protein) (non-patent document 10). IP7 produced by 5PPIP5K is 1-InsP$_7$, almost all parts of 127 in mammals are considered to be 5-isomer 5-InsP$_7$ (non-patent documents 3, 11).

Mammals have three IP6K subtypes of IP6K1, IP6K2, and IP6K3 (non-patent document 1), and recent studies using knockout mice have suggested the physiological role of each molecule and possibility as the target of drug discovery. The knockout mouse of IP6K1 has increased Akt signal in the liver, fat and muscle, and improvement of glucose tolerance, promotion of insulin sensitivity and increase in muscle amount have been confirmed under high-fat diet loading conditions (non-patent document 12). On the other hand, IP7 produced by IP6K2 has been reported to function as a major mediating molecule in cancer cell migration and tumor metastasis, and it has been confirmed that cellular infiltration and metastasis are suppressed by deficiency of IP6K2 in cancer cells (non-patent document 13). In addition, IP6K2 has been confirmed to have an action to promote cell death by producing IP7, and relation to neurodegenerative diseases such as amyotrophic lateral sclerosis and the like has been pointed out (non-patent document 14). IP6K3 is a molecule highly expressed in muscles. It has been confirmed that the gene expression thereof is induced by fasting and diabetic condition, the knockout mouse shows low blood glucose concentration and low blood insulin concentration, shows promoted glucose tolerance and promoted insulin sensitivity, and has a long life (non-patent document 15).

DOCUMENT LIST

Non-Patent Document non-patent document 1: Cell Mol Life Sci 66, 3851-3871, doi:10.1007/s00018-009-0115-2 (2009).
non-patent document 2: Adv Enzyme Regul 51, 74-82, doi:10.1016/j.advenzreg.2010.08.003 (2011).
non-patent document 3: J Biol Chem 284, 1863-1872, doi:10.1074/jbc.M805686200 (2009).
non-patent document 4: Curr Biol 9, 1323-1326 (1999).
non-patent document 5: Chem Biol 15, 274-286, doi: 10.1016/j.chembiol.2008.01.011 (2008).
non-patent document 6: J Biol Chem 282, 30763-30775, doi:10.1074/jbc.M704655200 (2007).
non-patent document 7: J Biol Chem 282, 30754-30762, doi:10.1074/jbc.M704656200 (2007).
non-patent document 8: Nat Chem Biol 8, 111-116, doi: 10.1038/n chembio.733 (2012).
non-patent document 9: Adv Biol Regul 57, 203-216, doi: 10.1016/j.jbior.2014.09.015 (2015).
non-patent document 10: Biochem J 452, 369-379, doi: 10.1042/BJ20130118 (2013).
non-patent document 11: Biochem J 327 (Pt 2), 553-560 (1997).
non-patent document 12: Cell 143, 897-910, doi:10.1016/j.cell.2010.11.032 (2010).
non-patent document 13: Proc Natl Acad Sci USA 112, 1773-1778, doi:10.1073/pnas.1424642112 (2015).
non-patent document 14: Mol Neurobiol 53, 5377-5383, doi:10.1007/s12035-015-9470-1 (2016).
non-patent document 15: Sci Rep 6, 32072, doi:10.1038/srep32072 (2016).

SUMMARY OF THE INVENTION

Problems to be Solved by the Invention

The present invention aims to provide a heterocyclic compound having an IP6K inhibitory action and expected to be useful as a prophylactic or therapeutic agent for diseases such as cardiac failure, diabetes and the like.

Means of Solving the Problems

The present inventors have found that the following compound represented by the formula (I) or a salt thereof (sometimes to be referred to as compound (I) in the present specification) has an IP6K inhibitory action, and conducted further studies, which resulted in the completion of the present invention.

Accordingly, the present invention is as described below.
[1] A compound represented by the formula:

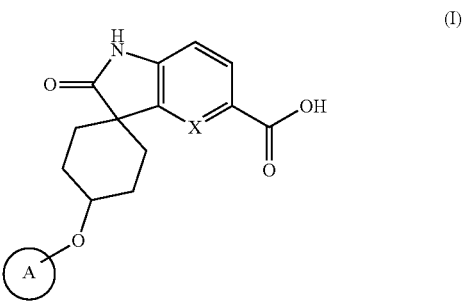

wherein
ring A is an optionally substituted aromatic ring;
X is CH or N
or a salt thereof.

[2] The compound of the above-mentioned [1], wherein the ring A is a $C_{6-14}$ aromatic hydrocarbon ring or a 5- to 14-membered aromatic heterocycle, each of which is optionally substituted by 1 to 3 substituents selected from
  (a) a halogen atom,
  (b) a cyano group,
  (c) a carbamoyl group,
  (d) an optionally halogenated $C_{1-6}$ alkyl group,
  (e) a $C_{1-6}$ alkoxy group,
  (f) a $C_{3-10}$ cycloalkyl group, and
  (g) a $C_{7-16}$ aralkyloxy group,
or a salt thereof.
[3] 4-((3,5-Dichloropyridin-2-yl)oxy)-2'-oxo-1',2'-dihydrospiro[cyclohexane-1,3'-indole]-5'-carboxylic acid or a salt thereof.
[4] 4-((3,5-dichloropyridin-2-yl)oxy)-2'-oxo-1',2'-dihydrospiro[cyclohexane-1,3'-pyrrolo[3,2-b]pyridine]-5'-carboxylic acid or a salt thereof.
[5] 2'-oxo-4-(2,4,6-trichlorophenoxy)-1',2'-dihydrospiro[cyclohexane-1,3'-indole]-5'-carboxylic acid or a salt thereof.
[6] 4-(2,4-dichlorophenoxy)-2'-oxo-1',2'-dihydrospiro[cyclohexane-1,3'-indole]-5'-carboxylic acid or a salt thereof.
[7] 4-((3-chloro-5-(trifluoromethyl)pyridin-2-yl)oxy)-2'-oxo-1',2'-dihydrospiro[cyclohexane-1,3'-indole]-5'-carboxylic acid or a salt thereof.
[8] 4-(4-chloro-2-methoxyphenoxy)-2'-oxo-1',2'-dihydrospiro[cyclohexane-1,3'-indole]-5'-carboxylic acid or a salt thereof.
[9] 4-((5-chloro-3-fluoropyridin-2-yl)oxy)-2'-oxo-1',2'-dihydrospiro[cyclohexane-1,3'-indole]-5'-carboxylic acid or a salt thereof.
[10] 4-(2,4-dichlorophenoxy)-2'-oxo-1',2'-dihydrospiro[cyclohexane-1,3'-pyrrolo[3,2-b]pyridine]-5'-carboxylic acid or a salt thereof.
[11] 4-((3-chloro-5-(trifluoromethyl)pyridin-2-yl)oxy)-2'-oxo-1',2'-dihydrospiro[cyclohexane-1,3'-pyrrolo[3,2-b]pyridine]-5'-carboxylic acid or a salt thereof.
[12] A medicament comprising the compound of the above-mentioned [1] or a salt thereof.
[13] The medicament of the above-mentioned [12], which is an inositol hexakisphosphate kinase (IP6K) inhibitor.
[14] The medicament of the above-mentioned [12], which is a prophylactic or therapeutic agent for a disease selected from cardiac failure and diabetes.
[15] A method for the prophylaxis or treatment of a disease selected from cardiac failure and diabetes in a mammal, comprising administering an effective amount of the compound of the above-mentioned [1] or a salt thereof to the mammal.
[16] A method for inhibiting inositol hexakisphosphate kinase in a mammal, comprising administering an effective amount of the compound of the above-mentioned [1] or a salt thereof to the mammal.
[17] Use of the compound of the above-mentioned [1] or a salt thereof in the production of a prophylactic or therapeutic agent for a disease selected from cardiac failure and diabetes.
[18] The compound of the above-mentioned [1] or a salt thereof for use in the prophylaxis or treatment of a disease selected from cardiac failure and diabetes.

Effect of the Invention

The compound of the present invention has an IP6K inhibitory action, and is expected to be useful as a prophylactic or therapeutic agent for diseases such as cardiac failure, diabetes and the like.

DETAILED DESCRIPTION OF THE INVENTION

Figure 1:
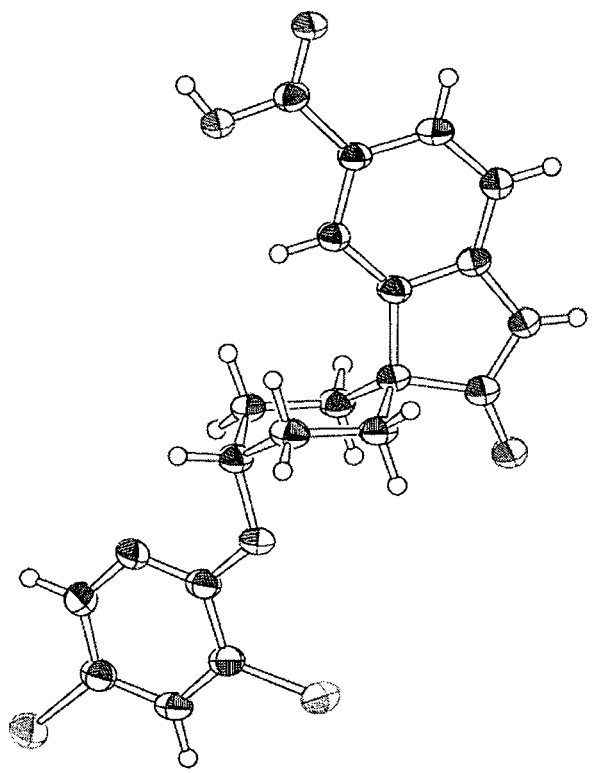
FIG. 1 shows a molecular structure of the compound of Example 9, obtained by single crystal X-ray structure analysis.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),

(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e. N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclyithiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane-, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

The definition of each symbol in the formula (I) is described in detail below.

Ring A is an optionally substituted aromatic ring.

The "aromatic ring" of the "optionally substituted aromatic ring" for ring A is, for example, a $C_{6-14}$ aromatic hydrocarbon ring (preferably benzene) or a 5- to 14-membered aromatic heterocycle (preferably, 5- or 6-membered monocyclic aromatic heterocycle (e.g., pyridine, pyrimidine, pyrazole)).

The "aromatic ring" of the "optionally substituted aromatic ring" for ring A is, for example, preferably benzene or a 5- or 6-membered monocyclic aromatic heterocycle (preferably pyridine, pyrimidine, pyrazole).

The "aromatic ring" of the "optionally substituted aromatic ring" for ring A may be condensed with, for example, a hydrocarbon ring or heterocycle.

The "aromatic ring" of the "optionally substituted aromatic ring" for ring A optionally has 1 to 5 (preferably 1 to 3) substituents at substitutable position(s), in addition to the substituent of the following formula

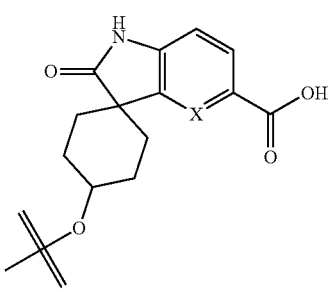

wherein X is CH or N. Examples of such substituent include the above-mentioned substituent group A. When a plurality of substituents are present, the respective substituents may be the same or different.

Ring A is preferably a $C_{6-14}$ aromatic hydrocarbon ring (e.g., benzene) or a 5- to 14-membered aromatic heterocycle (preferably 5- or 6-membered monocyclic aromatic heterocycle (e.g., pyridine, pyrimidine, pyrazole)), each of which is optionally substituted.

Ring A is more preferably a $C_{6-14}$ aromatic hydrocarbon ring (e.g., benzene) or a 5- to 14-membered aromatic heterocycle (preferably, 5- or 6-membered monocyclic aromatic heterocycle (e.g., pyridine, pyrimidine, pyrazole) which is optionally condensed with a 3- to 8-membered monocyclic non-aromatic heterocycle (e.g., dihydropyran) (e.g., dihydropyranopyridine)), each of which is optionally substituted by 1 to 3 substituents selected from
(a) a halogen atom (e.g., fluorine atom, chlorine atom),
(b) a cyano group,
(c) a carbamoyl group,
(d) an optionally halogenated $C_{1-6}$ alkyl group (e.g., methyl, trifluoromethyl),
(e) a $C_{1-6}$ alkoxy group (e.g., methoxy),
(f) a $C_{3-10}$ cycloalkyl group (e.g., cyclopropyl) and
(g) a $C_{7-16}$ aralkyloxy group (e.g., benzyloxy).

Ring A is further preferably
(1) a $C_{6-14}$ aromatic hydrocarbon ring (e.g., benzene) optionally substituted by 1 to 3 substituents selected from
(a) a halogen atom (e.g., fluorine atom, chlorine atom),
(b) a cyano group,
(c) a carbamoyl group,
(d) an optionally halogenated $C_{1-6}$ alkyl group (e.g., methyl, trifluoromethyl) and
(e) a $C_{1-6}$ alkoxy group (e.g., methoxy), or
(2) a 5- to 14-membered aromatic heterocycle (preferably, 5- or 6-membered monocyclic aromatic heterocycle (e.g., pyridine, pyrimidine, pyrazole), which is optionally condensed with a 3- to 8-membered monocyclic non-aromatic heterocycle (e.g., dihydropyran) (e.g., dihydropyranopyridine)) optionally substituted by 1 to 3 substituents selected from
(a) a halogen atom (e.g., fluorine atom, chlorine atom),
(b) a cyano group,
(c) an optionally halogenated $C_{1-6}$ alkyl group (e.g., methyl, trifluoromethyl),
(d) a $C_{3-10}$ cycloalkyl group (e.g., cyclopropyl) and
(e) a $C_{7-16}$ aralkyloxy group (e.g., benzyloxy).

Ring A is furthermore preferably benzene or a 5- or 6-membered monocyclic aromatic heterocycle (e.g., pyridine), each of which is optionally substituted by 1 to 3 substituents selected from
(a) a halogen atom (e.g., fluorine atom, chlorine atom),
(b) an optionally halogenated $C_{1-6}$ alkyl group (e.g., trifluoromethyl) and
(c) a $C_{1-6}$ alkoxy group (e.g., methoxy).

Ring A is still more preferably
(1) benzene substituted by 1 to 3 substituents selected from
(a) a halogen atom (e.g., chlorine atom) and
(b) a $C_{1-6}$ alkoxy group (e.g., methoxy), or
(2) a 5- or 6-membered monocyclic aromatic heterocycle (e.g., pyridine) substituted by 1 to 3 substituents selected from
(a) a halogen atom (e.g., fluorine atom, chlorine atom) and
(b) an optionally halogenated $C_{1-6}$ alkyl group (e.g., trifluoromethyl).

Ring A is particularly preferably pyridine substituted by 1 to 3 halogen atoms (e.g., chlorine atom).

X is CH or N.

A preferable embodiment of compound (I) includes the following compounds.

[Compound A]

Compound (I) wherein
ring A is a $C_{6-14}$ aromatic hydrocarbon ring (e.g., benzene) or a 5- to 14-membered aromatic heterocycle (preferably, 5- or 6-membered monocyclic aromatic heterocycle (e.g., pyridine, pyrimidine, pyrazole), which is optionally condensed with a 3- to 8-membered monocyclic non-aromatic heterocycle (e.g., dihydropyran) (e.g., dihydropyranopyridine)), each of which is optionally substituted by 1 to 3 substituents selected from
(a) a halogen atom (e.g., fluorine atom, chlorine atom),
(b) a cyano group,
(c) a carbamoyl group,
(d) an optionally halogenated $C_{1-6}$ alkyl group (e.g., methyl, trifluoromethyl),
(e) a $C_{1-6}$ alkoxy group (e.g., methoxy),
(f) a $C_{3-10}$ cycloalkyl group (e.g., cyclopropyl) and
(g) a $C_{7-16}$ aralkyloxy group (e.g., benzyloxy); and
X is CH or N.

[Compound B]

Compound (I) wherein
ring A is
(1) a $C_{6-14}$ aromatic hydrocarbon ring (e.g., benzene) optionally substituted by 1 to 3 substituents selected from
(a) a halogen atom (e.g., fluorine atom, chlorine atom),
(b) a cyano group,
(c) a carbamoyl group,
(d) an optionally halogenated $C_{1-6}$ alkyl group (e.g., methyl, trifluoromethyl) and
(e) a $C_{1-6}$ alkoxy group (e.g., methoxy), or
(2) a 5- to 14-membered aromatic heterocycle (preferably, 5- or 6-membered monocyclic aromatic heterocycle (e.g., pyridine, pyrimidine, pyrazole), which is optionally condensed with a 3- to 8-membered monocyclic non-aromatic heterocycle (e.g., dihydropyran) (e.g., dihydropyranopyridine)) optionally substituted by 1 to 3 substituents selected from
(a) a halogen atom (e.g., fluorine atom, chlorine atom),
(b) a cyano group,
(c) an optionally halogenated $C_{1-6}$ alkyl group (e.g., methyl, trifluoromethyl),
(d) a $C_{3-10}$ cycloalkyl group (e.g., cyclopropyl) and
(e) a $C_{7-16}$ aralkyloxy group (e.g., benzyloxy); and
X is CH or N.

[Compound C]

Compound (I) wherein
ring A is benzene or a 5- or 6-membered monocyclic aromatic heterocycle (e.g., pyridine), each of which is optionally substituted by 1 to 3 substituents selected from
(a) a halogen atom (e.g., fluorine atom, chlorine atom),
(b) an optionally halogenated alkyl group (e.g., trifluoromethyl) and
(c) a $C_{1-6}$ alkoxy group (e.g., methoxy); and
X is CH or N.

[Compound D]
Compound (I) wherein
ring A is
(1) benzene substituted by 1 to 3 substituents selected from
(a) a halogen atom (e.g., chlorine atom) and
(b) a $C_{1-6}$ alkoxy group (e.g., methoxy), or
(2) a 5- or 6-membered monocyclic aromatic heterocycle (e.g., pyridine) substituted by 1 to 3 substituents selected from
(a) a halogen atom (e.g., fluorine atom, chlorine atom) and
(b) an optionally halogenated $C_{1-6}$ alkyl group (e.g., trifluoromethyl); and
X is CH or N.
[Compound E]
Compound (I) wherein
ring A is pyridine substituted by 1 to 3 halogen atoms (e.g., chlorine atom); and
X is CH or N.

Specific examples of compound (I) include, for example, the compounds of the below-mentioned Examples 1-115.

When compound (I) is in a form of a salt, examples thereof include metal salts, an ammonium salt, salts with organic base, salts with inorganic acid, salts with organic acid, salts with basic or acidic amino acid, and the like. Preferable examples of the metal salt include alkali metal salts such as sodium salt, potassium salt and the like; alkaline earth metal salts such as calcium salt, magnesium salt, barium salt and the like; an aluminum salt, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salts with aspartic acid, glutamic acid and the like.

Among them, a pharmaceutically acceptable salt is preferable. For example, when a compound has an acidic functional group, examples thereof include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples thereof include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

The production method of the compound of the present invention is explained in the followings.

The raw material compound and reagent used and the compound obtained in each step in the following production method may be each in a form of a salt, and examples of such salt include those similar to the salts of the compound of the present invention and the like.

When the compound obtained in each step is a free form, it can be converted to the objective salt according to a method known per se. When the compound obtained in each step is a salt, it can be converted to the free form or the objective other salt according to a method known per se.

The compound obtained in each step can be used directly as the reaction solution or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature −300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;

ketones: acetone, methyl ethyl ketone and the like; water.

The above-mentioned solvent can be used in a mixture of two or more kinds thereof in an appropriate ratio.

When a base is used for the reaction in each step, examples thereof include those described in Examples and the following bases.
inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like;
Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & SonsInc); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for hydroxyl group such as alcohol or phenolic hydroxyl group include ether type protecting groups such as methoxymethyl ether, benzylether, tert-butyldimethylsilylether, tetrahydropyranylether and the like; carboxylate type protecting groups such as acetic acid ester and the like; sulfonic acid ester type protecting groups such as methanesulfonic acid ester and the like; carbonate type protecting groups such as tert-butylcarbonate and the like, and the like.

Examples of the protecting group for carbonyl group of aldehyde include acetal type protecting groups such as dimethylacetal and the like; cyclic acetal type protecting groups such as 1,3-dioxane and the like, and the like.

Examples of the protecting group for carbonyl group of ketone include ketal-type protecting groups such as dimethyl ketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for carboxyl group include ester-type protecting groups such as methyl ester and the like; amide-type protecting groups such as N,N-dimethylamide and the like, and the like.

Examples of the protecting group for thiol include ether-type protecting groups such as benzylthioether and the like; ester-type protecting groups such as thioacetic acid ester, thiocarbonate, thiocarbamate and the like, and the like.

Examples of the protecting group for amino group and aromatic hetero ring such as imidazole, pyrrole, indole and the like include carbamate-type protecting groups such as benzylcarbamate and the like; amide-type protecting groups such as acetamide and the like; alkylamine-type protecting groups such as N-triphenylmethylamine and the like, sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride, lithium tri-sec-butylborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (MCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like.

Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, examples of the reagent to be used include a combination of a Lewis acid and an acid chloride or a combination of a Lewis acid and an alkylating agent (e.g., an alkyl halide, an alcohol, an olefin etc.). Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., an organic base etc.) are used as the reagents.

When nucleophilic addition reaction by a carbo anion, nucleophilic 1,4-addition reaction (Michael addition reaction) by a carbo anion or nucleophilic displacement reaction by a carbo anion is carried out in each step, examples of the base to be used for generation of the carbo anion include organic lithiums, metal alkoxides, inorganic bases, organic bases and the like.

When Grignard reagent is carried out in each step, examples of the Grignard reagent to be used include arylmagnesium halides such as phenylmagnesium bromide and the like; and alkyl magnesium halides such as ethylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) azodicarboxylic acid bis(2-methoxyethyl) etc.) and triphenylphosphine are used as a reagent.

When esterification reaction, amidation reaction or ureaction reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two steps comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

Compound (I) can be produced from compound (1) or (4) according to the following method.

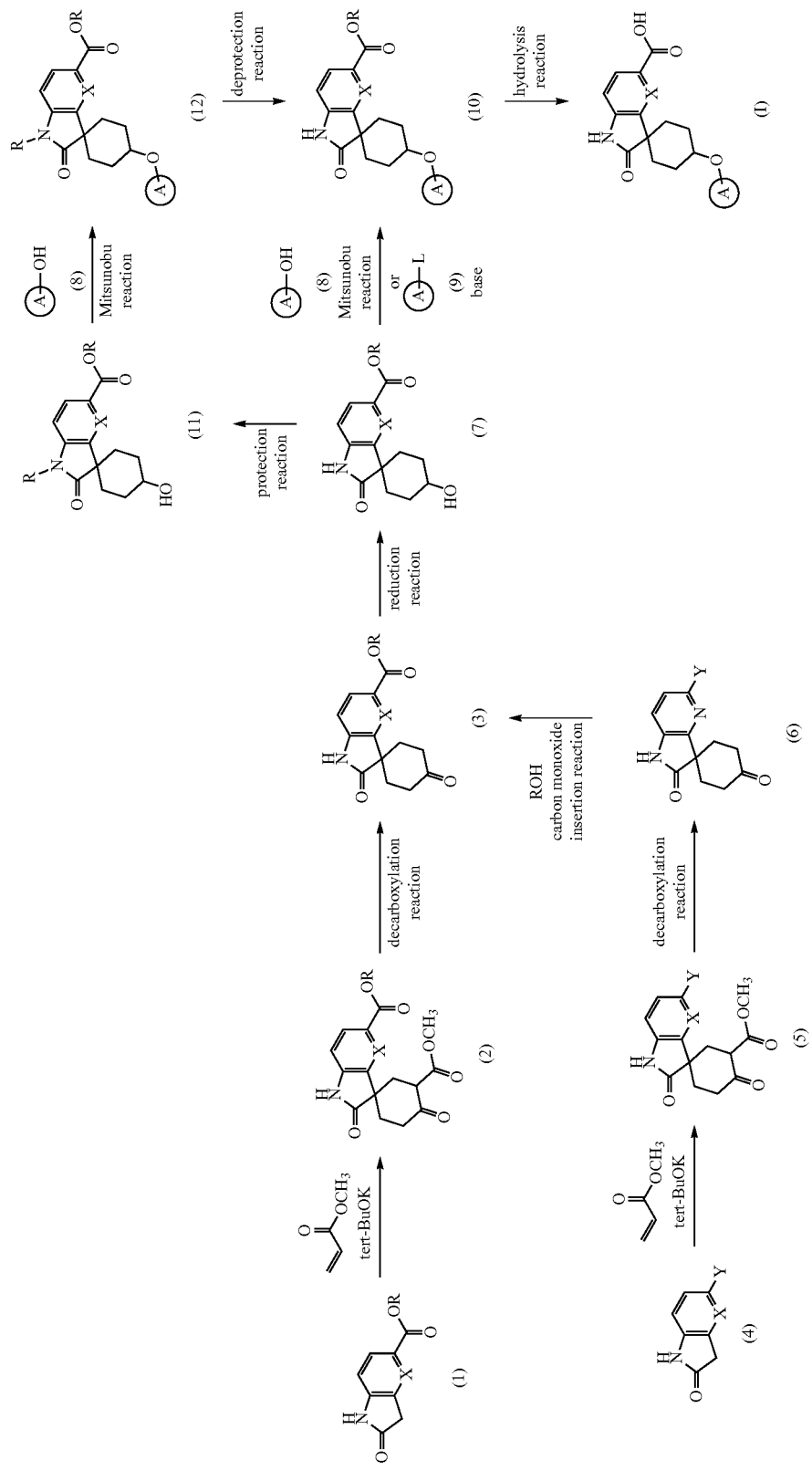

wherein R is a $C_{1-6}$ alkyl group, Y is a halogen atom (e.g., chlorine atom, bromine atom, iodine atom), L is a leaving group (e.g., halogen atom (e.g., fluorine atom, chlorine atom, bromine atom)), P is a protecting group, and other symbols are each as defined above.

Compound (2) can be produced by, for example, reacting compound (1) and methyl acrylate in the presence of an appropriate base such as potassium tert-butoxide.

Compound (3) can be produced by, for example, decarboxylation reaction by heating compound (2). An appropriate salt such as lithium chloride, sodium chloride, or an appropriate base such as sodium hydroxide may be added to the reaction system.

Compound (6) can be produced from compound (4) according to the production method of compound (3) from compound (1).

Compound (3) can also be produced by, for example, a carbon monoxide insertion reaction of compound (6) in the presence of alcohol. Examples of the palladium catalyst to be used include palladium(II) acetate, [1,1'-bis(diphenylphosphino)ferrocene]dichloropalladium(II) and the like. As the base, triethylamine and the like can be mentioned; as alcohol, methanol, ethanol and the like can be mentioned. Furthermore, a ligand such as 1,3-bis(diphenylphosphino) propane and the like may be added to the reaction.

Compound (7) can be produced by a reduction reaction of compound (3).

Compound (10) can be produced by Mitsunobu reaction of compound (7) and compound (8). It can also be produced by reacting compound (7) and compound (9) in the presence of an appropriate base such as sodium hydride, potassium tert-butoxide. In this case, an additive such as sodium iodide and potassium iodide may be added to the reaction.

Compound (10) can also be produced by protecting the nitrogen atom of compound (7) with an appropriate protecting group to give compound (11), performing Mitsunobu reaction of compound (11) and compound (8) to give compound (12), and deprotecting compound (12).

Compound (I) can be produced by hydrolyzing compound (10). Compounds (1), (4), (8) and (9) can be produced by a method known per se or a method according thereto.

When compound (I) has an optical isomer, a stereoisomer, a regioisomer or a rotamer, these are also encompassed in compound (I), and can be obtained as a single product according to a synthesis method and separation method known per se (e.g., concentration, solvent extraction, column chromatography, recrystallization etc.). For example, when compound (I) has an optical isomer, the optical isomer resolved from the compound is also encompassed in compound (I).

The optical isomer can be produced according to a method known per se. Specifically, the optical isomer is obtained using an optically active synthetic intermediate or by subjecting the racemic final product to an optical resolution according to a known method.

The optical resolution may be a method known per se, such as a fractional recrystallization method, a chiral column method, a diastereomer method etc.

1) Fractional Recrystallized Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallized method, and if desired, a neutralization step to give a free optical isomer.

2) Chiral Column Method

A method wherein a racemate or a salt thereof is applied to a column (a chiral column) for separation of an optical isomer to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, 2-propanol, acetonitrile, trifluoroacetic acid, diethylamine, etc.) as an eluent, solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallized method, a chromatography method etc.) and the like, and is subjected to a chemical treatment such as hydrolysis and the like to separate an optically active reagent moiety, whereby an optical isomer is obtained. For example, when compound (I) contains hydroxy or primary or secondary amino in a molecule, the compound and an optically active organic acid (e.g., MTPA [α-methoxy-α-(trifluoromethyl) phenylacetic acid], (−)-menthoxyacetic acid etc.) and the like are subjected to condensation reaction to give diastereomers of the ester compound or the amide compound, respectively. When compound (I) has a carboxy group, the compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis.

Compound (I) may be a crystal.

The crystal of compound (I) can be produced according to a crystallization method known per se.

Examples of the crystallization method include crystallization method from a solution, crystallization method from vapor, crystallization method from a melt, and the like.

The "crystallization method from a solution" is typically a method of shifting a non-saturated state to supersaturated state by varying factors involved in solubility of compounds (solvent composition, pH, temperature, ionic strength, redox state, etc.) or the amount of solvent. Specific examples thereof include a concentration method, a slow cooling method, a reaction method (a diffusion method, an electrolysis method), a hydrothermal growth method, a flux method and the like. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, 1,4-dioxane, etc.), nitriles (e.g., acetonitrile, etc.), ketones (e.g., acetone, etc.), sulfoxides (e.g., dimethyl sulfoxide, etc.), acid amides (e.g., N,N-dimethylformamide, etc.), esters (e.g., ethyl acetate, etc.), alcohols (e.g., methanol, ethanol, 2-propanol, etc.), water and the like. These solvents are used alone or in a combination of two or more at a suitable ratio (e.g., 1:1 to 1:100 (a volume ratio)). Where necessary, a seed crystal can be used.

The "crystallization method from vapor" is, for example, a vaporization method (a sealed tube method, a gas stream method), a gas phase reaction method, a chemical transportation method and the like.

The "crystallization method from a melt" is, for example, a normal freezing method (a pulling method, a temperature gradient method, a Bridgman method), a zone melting method (a zone leveling method, a floating zone method), a special growth method (a VLS method, a liquid phase epitaxy method) and the like.

Preferable examples of the crystallization method include a method comprising dissolving compound (I) in a suitable solvent (e.g., alcohols such as methanol, ethanol etc.) at 20° C. to 120° C., and cooling the obtained solution to a temperature (e.g., 0 to 50° C., preferably 0 to 20° C.) not higher than the dissolution temperature, and the like.

The thus-obtained crystals of the present invention can be isolated, for example, by filtration and the like.

An analysis method of the obtained crystal is generally a method of crystal analysis by powder X-ray diffraction. As a method of determining crystal orientation, a mechanical method or an optical method and the like can also be used.

The crystal of compound (I) obtained by the above-mentioned production method may have high purity, high quality, and low hygroscopicity, may not be denatured even after a long-term preservation under general conditions, and may be expected to be superior in the stability. In addition, it may be also superior in the biological properties (e.g., pharmacokinetics (absorption, distribution, metabolism, excretion), efficacy expression etc.) and may be extremely useful as a medicament.

The prodrug of compound (I) means a compound which is converted to compound (I) with a reaction due to an enzyme, gastric acid and the like under the physiological condition in the living body, that is, a compound which is converted to compound (I) by enzymatic oxidation, reduction, hydrolysis and the like; a compound which is converted to compound (I) by hydrolysis and the like due to gastric acid, and the like. Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation, tert-butylation, and the like); a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation, and the like); a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, and the like) and the like. These compounds can be produced from compound (I) according to a method known per se.

The prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, compound (I) and the prodrug of compound (I) are sometimes collectively abbreviated as "the compound of the present invention".

Compound (I) may be a hydrate, a non-hydrate, a solvate or a non-solvate.

In addition, compound (I) may be a compound labeled or substituted with an isotope (e.g., $^2H$, $^3H$, $^{11}C$, $^{14}C$, $^{18}F$, $^{35}S$, $^{125}I$ and the like) and the like. The compound labeled or m substituted with an isotope may be used, for example, as a tracer (PET tracer) used in positron emission tomography (PET), and useful in the field of medical diagnosis and the like.

Compound (I) also encompasses a deuterium conversion form wherein $^1H$ is converted to $^2H(D)$.

Compound (I) also encompasses a tautomer thereof.

Compound (I) may be a pharmaceutically acceptable cocrystal or a salt thereof. The cocrystal or a salt thereof means a crystalline substance constituted with two or more special solids at room temperature, each having different physical properties (e.g., structure, melting point, melting heat, hygroscopicity, solubility and stability etc.). The cocrystal or a salt thereof can be produced according to a cocrystallization a method known per se.

Compound (I) may also be used as a PET tracer.

Since the compound of the present invention has a superior IP6K inhibitory action, it may also be useful as a safe medicament based on this action.

For example, the medicament of the present invention containing the compound of the present invention may be expected to show low toxicity (e.g., acute toxicity, chronic toxicity, genetic toxicity, reproductive toxicity, cardiotoxicity, carcinogenicity), and used for a mammal (e.g., mouse, rat, hamster, rabbit, cat, dog, bovine, sheep, monkey, human etc.) as a prophylactic or therapeutic agent for diseases involving IP6K.

To be specific, the compound of the present invention can be used as an agent for the prophylaxis or treatment of diabetes (e.g., type 1 diabetes, type 2 diabetes, gestational diabetes, obese diabetes), cardiovascular disease (e.g., cardiac failure, arrhythmia, ischemic cardiac diseases, heart valvular disease, arteriosclerosis), obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity etc.), non-alcoholic fatty liver diseases (NAFLD), non-alcoholic steatohepatitis (NASH), hyperphagia, hyperlipidemia/dyslipidemia (e.g., hypertriglyceridemia, hypercholesterolemia, high LDL-cholesterolemia, hypo HDL-cholesterolemia, postprandial hyperlipemia), Hyperphosphatemia, hypophosphatemia, Hyperkalemia, hypertension, diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia hypacusis, hypacusis, cerebrovascular diseases, peripheral blood circulation disorder], metabolic syndrome (pathology with not less than 3 selected from hyper-triglycerid(TG)emia, hypo HDL cholesterol(HDL-C)emia, hypertension, abdomen obesity and impaired glucose tolerance), sarcopenia, emotional disorder, sexual dysfunction, depression, anxiety, neurosis, arteriosclerosis, gonitis, acute renopathy, glaucoma, ischemic disease, myocardial infarction, cerebral apoplexy, dementia, Neurodegenerative diseases [e.g., amyotrophic lateral sclerosis], mitochondria disease, Retinitis pigmentosa, glaucoma, Osteoporosis, fungi infections and the like.

For diagnostic criteria of diabetes, Japan Diabetes Society issued "Report of the Committee on the Classification and Diagnostic Criteria of Diabetes Mellitus" in 2010.

According to this report, diabetes is a condition showing any of a fasting blood glucose level (glucose concentration of intravenous plasma) of not less than 126 mg/dL, a 75 g oral glucose tolerance test (75 g OGTT) 2 h level (glucose concentration of intravenous plasma) of not less than 200 mg/dL, a non-fasting blood glucose level (glucose concentration of intravenous plasma) of not less than 200 mg/dL and HbAlc (international standard value) of not less than 6.5%. HbAlc (international standard value) (%) is indicated as a value equivalent to the internationally standardized NGSP (National Glycohemoglobin Standardization Program), which is a value of HbAlc (JDS value) (%) expressed by conventional JDS (Japan Diabetes Society) value plus 0.4% thereof. A condition not falling under the above-mentioned diabetes and different from "a condition showing a fasting blood glucose level (glucose concentration of intravenous plasma) of less than 110 mg/dL or a 75 g oral glucose tolerance test (75 g OGTT) 2 h level (glucose concentration of intravenous plasma) of less than 140 mg/dL" (normal type) is called a "borderline type".

According to the reports from WHO (World Health Organization) in 2006, diabetes is a condition showing a fasting blood glucose level (glucose concentration of intravenous plasma) of not less than 126 mg/dL, or a 75 g oral glucose tolerance test 2 h level (glucose concentration of intravenous plasma) of not less than 200 mg/dL.

According to the above-mentioned reports, impaired glucose tolerance (IGT) is a condition showing a fasting blood glucose level (glucose concentration of intravenous plasma) of not less than 126 mg/dL and a 75 g oral glucose tolerance test 2 h level (glucose concentration of intravenous plasma) of not less than 140 mg/dL and less than 200 mg/dL. According to the report of WHO, a condition showing a fasting blood glucose level (glucose concentration of intravenous plasma) of not less than 110 mg/dL and less than 126 mg/dL and, if a measurement value exists, a 75 g oral glucose tolerance test 2 h level glucose concentration of intravenous plasma) of less than 140 mg/dL is called IFG (Impaired Fasting Glucose).

The compound of the present invention can also be used as an agent for the prophylaxis or treatment of diabetes, borderline type, impaired glucose tolerance or IFG (Impaired Fasting Glucose), as judged according to the above-mentioned reports. Moreover, the compound of the present invention can also prevent progress of borderline type, impaired glucose tolerance or IFG (Impaired Fasting Glucose) into diabetes.

The clinical condition of cardiac failure is classified into 4 stages shown in Table 1 according to the severity by the New York Heart Association (NYHA).

TABLE 1

| NYHA classification of cardiac failure | |
|---|---|
| level | symptom of patient |
| level I | Cardiac disease, but no limitation of physical activity. Ordinary physical activity does not cause undue fatigue, palpitation, dyspnea or anginal pain. |

TABLE 1-continued

| NYHA classification of cardiac failure | |
|---|---|
| level | symptom of patient |
| level II | Slight limitation of physical activity. No symptom at rest. Ordinary physical activity results in fatigue, palpitation, dyspnea or angina pain. |
| level III | Marked limitation of physical activity. No symptom at rest. Less than ordinary activity causes fatigue, palpitation, dyspnea or angina pain. |
| level IV | All physical activities are limited due to cardiac disease. Cardiac failure symptoms and angina pain exist even at rest. A small effort aggravates these symptoms. | level IIs: Slight limitation of physical activity
level IIm: Moderate limitation of physical activity The AHA/ACC stage classification (American Heart Association/American college of cardiology) divides into 4 stages shown in Table 2 according to the severity.

TABLE 2

| AHA/ACC stage classification of cardiac failure | |
|---|---|
| stage | definition |
| A | with risk factor but no cardiac dysfunction |
| B | left ventricular systolic dysfunction without symptom |
| C | symptomatic heart failure |
| D | intractable cardiac failure |

The NYHA classification and AHA/ACC stage classification generally correspond to each other as shown in the following Table 3.

TABLE 3

| corresponding relation between NYHA classification and AHA/ACC stage classification | |
|---|---|
| NYHA classification | AHA/ACC stage classification |
| — | A |
| level I | B |
| level II | C |
| level III | |
| level IV | |
| level IV | D |

The compound of the present invention is also used as a prophylactic or therapeutic agent for cardiac failure, low cardiac output, ischemic cardiac failure, non-ischemic cardiac failure, decompensated cardiac failure, acute cardiac failure or acute decompensated cardiac failure, judged by the above-mentioned reports.

The compound of the present invention can also be used for improving low ejection fraction or increasing ejection fraction in subjects with cardiac failure.

The compound of the present invention can also suppress aggravation of cardiac function or suppress progression of aggravation in subjects with cardiac failure. The compound of the present invention can also reduce load on the heart, suppress cardiac hypertrophy, suppress stromafibrosis and suppress increase of apoptosis in subjects with cardiac failure.

The compound of the present invention is also useful as an agent for the prophylaxis or treatment of metabolic syndrome. Because patients with metabolic syndrome have an extreme high incidence of cardiovascular diseases as compared to patients with single lifestyle-related disease, the prophylaxis or treatment of metabolic syndrome is quite important to prevent cardiovascular diseases.

Criteria for diagnosis of metabolic syndrome are announced by WHO in 1999, and by NCEP in 2001. According to the criterion of WHO, patients with at least two of abdominal obesity, dyslipidemia (high TG or low HDL) and hypertension in addition to hyperinsulinemia or impaired glucose tolerance are diagnosed as metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the criterion of Adult Treatment Panel III of National Cholesterol Education Program, that is an indicator for managing ischemic heart diseases in America, patients with at least three of abdominal obesity, hypertriglyceridemia, hypo HDL cholesterolemia, hypertension and impaired glucose tolerance are diagnosed as metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compound of the present invention can also be used for the secondary prevention and the suppression of progression of the above-mentioned various diseases (e.g., cardiovascular event such as myocardial infarction and the like).

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

A medicament containing the compound of the present invention may be able to use the compound of the present invention solely or as a pharmaceutical composition of the compound of the present invention mixed with a pharmacologically acceptable carrier according to a method known per se (e.g., the method described in the Japanese Pharmacopoeia etc.) as the production method of a pharmaceutical preparation. The medicament containing the compound of the present invention may be able to be administered safely as, for example, tablet (including sugar-coated tablet, film-coated tablet, sublingual tablet, orally disintegrating tablet, buccal etc.), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, cream, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor and direct administration to the lesion).

The content of the compound of the present invention in the medicament of the present invention is about 0.01 to 100% by weight of the entire medicament. The dose may vary depending on administration subject, administration route, disease and the like. For example, for oral administration to patients (body weight about 60 kg) with diabetes, about 0.01 mg/kg body weight-about 500 mg/kg body weight, preferably about 0.1 mg/kg body weight-about 50 mg/kg body weight, more preferably about 1 mg/kg body weight-about 30 mg/kg body weight of an active ingredient (compound (I)) may be administered once to several portions per day.

The pharmaceutically acceptable carrier, which may be used for the production of the medicament of the present invention, may be exemplified by various organic or inorganic carrier materials that are conventionally used as preparation materials, for example, excipient, lubricant, binding agent and disintegrant for solid preparations; or solvent, solubilizing agent, suspending agent, isotonic agent, buffering agent, soothing agent and the like for liquid preparations. Furthermore, when necessary, ordinary additives such as preservative, antioxidant, colorant, sweetening agent, adsorbing agent, wetting agent and the like can also be used as appropriate in an appropriate amount.

The dose of the pharmaceutical composition of the present invention as a sustained-release preparation varies depending on the kind and content of compound (I), dosage form, period of sustained drug release, subject animal of administration (e.g., mammals such as mouse, rat, hamster, guinea pig, rabbit, cat, dog, bovine, horse, swine, sheep, monkey, human etc.), and administration object. For example, for application by parenteral administration, about 0.1 to about 100 mg of compound (I) needs to be released from the administered preparation per 1 week.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidant include sulfites, ascorbic acid, α-tocopherol and the like.

For the prophylaxis or treatment of various diseases, the compound of the present invention may also be used together with other medicaments. In the following, a medicament to be used when the compound of the present invention is used together with other drug is referred to as "the combination agent of the present invention".

For example, the compound of the present invention may be used together with the following drugs (concomitant drugs).

(1) Therapeutic Agent for Diabetes insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO2007/013694, WO2007/018314, WO2008/093639 and WO2008/099794), α-glucosidase inhibitors (e.g., voglibose, acarbose, miglitol, emiglitate), biguanides (e.g., metformin or a salt thereof (preferably hydrochloride), buformin or a salt thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], dipeptidylpeptidase IV inhibitors (e.g., Alogliptin or a salt thereof (preferably benzoate), Vildagliptin, Sitagliptin, Saxagliptin, Teneligliptin, Linagliptin, Anagliptin, Melogliptin, Dutogliptin, PF-00734200, ALS2-0426, TA-6666, TS-021, KRP-104, Trelagliptin or a salt thereof (preferably succinic acid salt)), β3 agonists (e.g., N-5984), GPR40 agonist (e.g., fasiglifam, compound described in WO2004/041266, WO2004/106276, WO2005/063729, WO2005/063725, WO2005/087710, WO2005/095338, WO2007/013689 or WO2008/001931), GLP-1 receptor agonist [e.g., GLP-1, GLP-1MR agent, Liraglutide, Exenatide, AVE-0010, BIM-51077, Aib(8,35)hGLP-1(7,37)NH2, CJC-1131, Albiglutide], semaglutide, amylin agonist (e.g., pramlintide), phosphotyrosine phosphatase inhibitors (e.g., sodium vanadate), gluconeogenesis inhibitor (e.g., glycogen phosphorylase inhibitor, glucose-6-phosphatase inhibitor, glucagon antagonist, FBPase inhibitor), SGLT2 (sodium-glucose cotransporter 2) inhibitor (e.g., ipragliflozin, dapagliflozin, luseogliflozin, tofogliflozin, canagliflozin, empagliflozin, AVE2268, TS-033, YM543, TA-7284, Remogliflozin, ASP1941), SGLT1 inhibitor, 11p-hydroxysteroid dehydrogenase inhibitor (e.g., BVT-3498), adiponectin or agonist thereof, IKK inhibitor (e.g., AS-2868), leptin resistance improving drugs, somatostatin receptor agonists, glucokinase activators (e.g., Piragliatin, AZD1656, AZD6370, TTP-355, compound described in WO2006/112549, WO2007/028135, WO2008/047821, WO2008/050821, WO2008/136428 or WO2008/156757), GIP (Glucose-dependent insulinotropic peptide) and the like.

(2) Therapeutic Agent for Diabetic Complications aldose reductase inhibitors (e.g., Tolrestat, Epalrestat, Zopolrestat, Fidarestat, CT-112, ranirestat (AS-3201), Lidorestat), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy) propyl]oxazole), compound described in WO2004/039365)), nerve regeneration promoting drugs (e.g., Y-128), PKC inhibitors (e.g., ruboxistaurin mesylate), AGE inhibitors (e.g., ALT-946, pyratoxanthine, N-phenacylthiazolium bromide (ALT-766), ALT-711, EXO-226, Pyridorin, Pyridoxamine), GABA receptor agonists (e.g., gabapentin, Pregabalin), serotonin.noradrenaline reuptake inhibitors (e.g., duloxetine), sodium channel inhibitors (e.g., Lacosamide), active oxygen scavengers (e.g., thioctic acid), cerebral vasodilators (e.g., tiapuride, mexiletine), somatostatin receptor agonists (BIM23190), apoptosis signal regulating kinase-1 (ASK-1) inhibitors and the like.

(3) Therapeutic Drug for Cardiac Failure (i) β receptor antagonists carvedilol, metoprolol, atenolol and the like.

(ii) diuretic drug hydrochlorothiazide, spironolactone, furosemide, indapamide, bendrofluazide, cyclopenthiazide and the like.

(iii) cardiotonic drug digoxin, dobutamine and the like.

(iv) antialdosterone drug spironolactone, eplerenone and the like.

(v) heart rate-lowering drug ivabradine and the like.

(vi) intravenous cardiotonic injection h-ANP and the like.

(vii) others relaxin and the like.

(4) Others (viii) Ca sensitizer

MCC-135 and the like.

(ix) Ca channel antagonist nifedipine, diltiazem, verapamil, lomerizine hydrochloride, amlodipine besylate and the like.

(x) anti-platelet drug, anticoagulator heparin, aspirin, warfarin, dabigatran, rivaroxaban, apixaban, edoxaban and the like.

(xi) HMG-CoA reductase inhibitor atorvastatin, simvastatin and the like.

(xii) hypouricemic drug probenecid, allopurinol, febuxostat and the like.

(xiii) α-blocker doxazosin and the like.

(xiv) oral adsorptive agent kremezin and the like.

(xv) therapeutic drug for hyperkalemia

*calcicol* and the like.

(xvi) therapeutic drug for hyperphosphatemia sevelamer, lanthanum carbonate and the like.

(xvii) metabolic acidosis improving drug sodium bicarbonate and the like.

(xviii) activity type vitamin

For combined use, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:
(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention m and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-about 100 wt %, preferably about 0.1-about 50 wt %, more preferably about 0.5-about 20 wt %, of the whole preparation.

The content of the concomitant drug in the combination agent of the present invention varies depending on the preparation form, and generally about 0.01 to about 100% by weight, preferably about 0.1 to about 50% by weight, further preferably about 0.5 to about 20% by weight, of the whole preparation.

While the content of the additive such as a carrier and the like in the combination agent of the present invention varies depending on the form of a preparation, it is generally about 1 to about 99.99% by weight, preferably about 10 to about 90% by weight, based on the whole preparation.

When the compound of the present invention and the concomitant drug are separately prepared, the same content may be adopted.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to about 2000 mg, preferably about 0.01 to about 500 mg, further preferably about 0.1 to about 100 mg, per 1 kg of a mammal and this is generally administered once to 4-times, divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

The elution by column chromatography in the Examples was performed under observation by TLC (thin layer chromatography), unless otherwise specified. In TLC observation, 60 $F_{254}$ manufactured by Merck was used as TLC plate and, as the eluent, the solvent used as an elution solvent in column chromatography was used. For detection, UV detector was employed. In silica gel column chromatography, "NH" means use of aminopropylsilane-bound silica gel and "Diol" means use of 3-(2,3-dihydroxypropoxy)propylsilane-bound silica gel. In preparative HPLC (high performance liquid chromatography), "C18" means use of octadecyl-bound silica gel. The ratios of elution solvents are volume mixing ratios, unless otherwise specified.

For the analysis of $^1$H NMR, ACD/SpecManager (trade name) software and the like were used. Peaks of a hydroxy group, an amino group and the like, which having very mild proton peaks, are not described sometimes.

MS was measured by LC/MS. As an ionization method, ESI method or APCI method was used. The data indicates those found. Generally, a molecular ion peak is observed but it may be observed as a fragment ion. In the case of a salt, a molecular ion peak or fragment ion peak of free form is generally observed.

The unit of sample concentration (c) in optical rotation ($[\alpha]_D$) is g/100 mL.

As the elemental analysis values (Anal.), calculated values (Calcd) and measured values (Found) are described.

In the Examples, the peak by a powder X-ray diffraction means a peak measured at room temperature using Ultima IV (Rigaku Corporation, Japan) with a Cu-Kα ray as a ray source. The measurement conditions are as follows.
Electric pressure/Electric current: 40 kV/50 mA
Scan speed: 6 degree/min
Scan range of 2 Theta: 2-35 degree
The crystallinity by powder X-ray diffraction in the Examples was calculated by the Hermans method.

The X-ray crystal structure analysis in the Examples included measurement of diffraction data by XtaLAB P200 manufactured by Rigaku Corporation. The initial phase was determined by the direct method (SIR2008 (Burla, M. C.; Caliandro, R.; Camalli, M.; Carrozzini, B.; Cascarano, G. L.; De Caro, L.; Giacovazzo, C.; Polidori, G.; Siliqi, D.; Spagna, R. SIR2008: Program for the Solution of Crystal Structures from X-ray Data; CNR Institute of Crystallography: Bari, Italy, 2007.)) and the structure was refined using the full-matrix least-squares method (SHELXL-2014/7 (Sheldrick, G. M. Acta Cryst. A 2008, 64, 112-122.)). An anisotropic temperature factor was applied to non-hydrogen atoms and an isotropic temperature factor was applied to a hydrogen atom.

In Examples, the following abbreviations are used.
mp: melting point
MS: mass spectrum
M: mol concentration
N: normality
$CDCl_3$: deuterochloroform
DMSO-$d_6$: deuterodimethyl sulfoxide
$CD_3OD$: deuterated methanol
$^1$H NMR: proton nuclear magnetic resonance
LC/MS: liquid chromatograph mass spectrometer
ESI: electrospray ionization
APCI: atmospheric pressure chemical ionization
TFA: trifluoroacetic acid Example 1

(1r,4r)-4-(2,4-dichlorophenoxy)-2'-oxo-1',2'-dihydrospiro[cyclohexane-1,3'-indole]-5'-carboxylic Acid A) dimethyl 2',4-dioxo-1',2'-dihydrospiro[cyclohexane-1,3'-indole]-3,5'-dicarboxylate To a mixture of methyl 2-oxoindoline-5-carboxylate (57.4 g), potassium tert-butoxide (1.68 g) and dimethyl sulfoxide (300 ml) was added methyl acrylate (81 ml) at 40° C. over 1 hr. At that time, the internal temperature rose to 60° C. The reaction mixture was stirred under a nitrogen atmosphere at 60° C. for 30 min, and potassium tert-butoxide (20.3 g) was added 4 times (total amount 81 g) at 10 min intervals. The reaction mixture was stirred under a nitrogen atmosphere at 60° C. for 1 hr, neutralized with 6N hydrochloric acid at 10° C.–15° C., and extracted with ethyl acetate. The organic layer was separated, washed with water, saturated aqueous sodium hydrogen carbonate solution and saturated brine, dried over anhydrous magnesium sulfate and concentrated under reduced pressure. The residue was washed with ethyl acetate-hexane (1:4) to give the title compound (72.0 g).
MS: [M–H]$^-$ 330.0.

B) methyl 2',4-dioxo-1',2'-dihydrospiro[cyclohexane-1,3'-indole]-5'-carboxylate

A mixture of dimethyl 2',4-dioxo-1',2'-dihydrospiro[cyclohexane-1,3'-indole]-3,5'-dicarboxylate (105 g), water (5.71 ml), sodium chloride (18.5 g) and dimethyl sulfoxide (400 ml) was stirred at 150° C. for 5 hr. The reaction mixture was poured into water, and the mixture was extracted with ethyl acetate. The organic layer was separated, washed with water and saturated brine, dried over anhydrous magnesium sulfate and concentrated under reduced pressure. The residue was washed with ethyl acetate to give the title compound (55.2 g).
MS: [M–H]$^-$ 272.0.

C) methyl (1s,4s)-4-hydroxy-2'-oxo-1',2'-dihydrospiro[cyclohexane-1,3'-indole]-5'-carboxylate (I) and methyl (1r,4r)-4-hydroxy-2'-oxo-1',2'-dihydrospiro[cyclohexane-1,3'-indole]-5'-carboxylate (II)

To a solution of methyl 2',4-dioxo-1',2'-dihydrospiro[cyclohexane-1,3'-indole]-5'-carboxylate (3.05 g) in tetrahydrofuran (75 ml) was added sodium borohydride (0.844 g) at 0° C., and the mixture was stirred at room temperature overnight. To the reaction mixture was added 1N hydrochloric acid at room temperature, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (I) (1.35 g) and the title compound (II) (110 mg).
Title Compound (I)
$^1$H NMR (400 MHz, DMSO-$d_6$) δ 1.60-1.82 (6H, m), 1.87-2.03 (2H, m), 3.71-3.78 (1H, m), 3.81 (3H, s), 4.59 (1H, d, J=4.0 Hz), 6.92 (1H, d, J=8.8 Hz), 7.82-7.86 (2H, m), 10.65 (1H, d, J=1.0 Hz). MS: [M–H]$^-$ 274.0.
Title Compound (II)
$^1$H NMR (400 MHz, DMSO-$d_6$) 51.56-1.73 (6H, m), 1.98-2.02 (2H, m), 3.68 (1H, brs), 3.83 (3H, s), 4.83 (1H, d, J=4.1 Hz), 6.97 (1H, d, J=8.3 Hz), 7.88 (1H, dd, J=8.2, 1.3 Hz), 8.02 (1H, d, J=1.0 Hz), 10.78 (1H, brs). MS: [M–H]$^-$ 274.0.

D) methyl (1r,4r)-4-(2,4-dichlorophenoxy)-2'-oxo-1',2'-dihydrospiro[cyclohexane-1,3'-indole]-5'-carboxylate To a mixture of diisopropyl azodicarboxylate (1.9 mol/l toluene solution, 2.87 ml), triphenylphosphine (1.43 g) and tetrahydrofuran (20 ml) was added 2,4-dichlorophenol (0.711 g) at room temperature, and a solution of methyl (1s,4s)-4-hydroxy-2'-oxo-1',2'-dihydrospiro[cyclohexane-1,3'-indole]-5'-carboxylate (1.00 g) in tetrahydrofuran (20 ml) was added. After stirring at room temperature overnight, water was added to the mixture and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (1.37 g) as a crude purified product. MS: [M–H]$^-$ 418.1.

E) (1r,4r)-4-(2,4-dichlorophenoxy)-2'-oxo-1',2'-dihydrospiro[cyclohexane-1,3'-indole]-5'-carboxylic Acid To a mixture of methyl (1r,4r)-4-(2,4-dichlorophenoxy)-2'-oxo-1',2'-dihydrospiro[cyclohexane-1,3'-indole]-5'-carboxylate (1.37 g), tetrahydrofuran (15 ml) and methanol (15 ml) was added 2N aqueous sodium hydroxide solution (16.3 ml) at room temperature. The mixture was stirred at 50° C. overnight and concentrated under reduced pressure. The residue was diluted with water, the aqueous layer was washed with ethyl acetate, neutralized with 6N hydrochloric acid, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) and the obtained solid was crystallized from methanol/water to give the title compound (320 mg).

1H NMR (400 MHz, DMSO-$d_6$) δ 1.69 (2H, dd, J=11.1, 6.2 Hz), 1.82-1.98 (4H, m), 2.23-2.37 (2H, m), 4.85 (1H, brs), 6.94 (1H, d, J=8.0 Hz), 7.37 (2H, s), 7.62 (1H, s), 7.85 (1H, d, J=8.2 Hz), 7.89 (1H, s), 10.72 (1H, s), 12.68 (1H, brs).

Example 3

(1r,4r)-2'-oxo-4-(2,4,6-trichlorophenoxy)-1',2'-dihydrospiro[cyclohexane-1,3'-indole]-5'-carboxylic Acid A) methyl (1r,4r)-2'-oxo-4-(2,4,6-trichlorophenoxy)-1',2'-dihydrospiro[cyclohexane-1,3'-indole]-5'-carboxylate To a mixture of diisopropyl azodicarboxylate (1.9 mol/l toluene solution, 0.287 ml), triphenylphosphine (143 mg) and tetrahydrofuran (4 ml) were added 2,4,6-trichlorophenol (86 mg) and methyl (1s,4s)-4-hydroxy-2'-oxo-1',2'-dihydrospiro[cyclohexane-1,3'-indole]-5'-carboxylate (100 mg) at room temperature, and the mixture was stirred at the same temperature for 60 hr. To the reaction mixture was added water at room temperature and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (260 mg) as a crude purified product. MS: [M–H]⁻ 452.0.

B) (1r,4r)-2'-oxo-4-(2,4,6-trichlorophenoxy)-1',2'-dihydrospiro[cyclohexane-1,3'-indole]-5'-carboxylic Acid To a mixture of methyl (1r,4r)-2'-oxo-4-(2,4,6-trichlorophenoxy)-1',2'-dihydrospiro[cyclohexane-1,3'-indole]-5'-carboxylate (165 mg), tetrahydrofuran (2 ml) and methanol (2 ml) was added 2N aqueous sodium hydroxide solution (1.81 ml) at room temperature and the mixture was stirred at 50° C. overnight. The reaction mixture was concentrated under reduced pressure, and water and ethyl acetate were added to the residue. The aqueous layer was separated, neutralized with 6N hydrochloric acid, and the mixture was extracted with ethyl acetate. The organic layer was separated, washed with saturated brine, dried over anhydrous magnesium sulfate and concentrated under reduced pressure. The residue was washed with heated ethanol to give the title compound (115 mg).

$^1$H NMR 400 MHz, DMSO-$d_6$) δ 1.67-1.89 (4H, m), 1.99-2.09 (2H, m), 2.19 (2H, d, J=5.6 Hz), 4.53-4.63 (1H, m), 6.91-7.00 (1H, m), 7.73 (2H, s), 7.88 (1H, d, J=8.2 Hz), 8.06 (1H, s), 10.79 (1H, s), 12.68 (1H, brs).

Example 4

(1r,4r)-4-((3,5-difluoropyridin-2-yl)oxy)-2'-oxo-1',2'-dihydrospiro[cyclohexane-1,3'-indole]-5'-carboxylic Acid A) methyl (1r,4r)-4-((3,5-difluoropyridin-2-yl)oxy)-2'-oxo-1',2'-dihydrospiro[cyclohexane-1,3'-indole]-5'-carboxylate To a mixture of methyl (1r,4r)-4-hydroxy-2'-oxo-1',2'-dihydrospiro[cyclohexane-1,3'-indole]-5'-carboxylate (1.50 g) and N,N-dimethylformamide (50 ml) was added sodium hydride (60% in oil, 436 mg) at 0° C., and the mixture was stirred at the same temperature for 30 min and 2,3,5-trifluoropyridine (1.09 g) was added. After stirring at room temperature for 10 hr, the reaction mixture was poured into ice water and extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) to give the title compound (500 mg).

$^1$H NMR (400 MHz, DMSO-$d_6$) δ 1.77-1.95 (6H, m), 2.33-2.34 (2H, m), 3.85 (3H, s), 5.28-5.27 (1H, m), 6.99-7.01 (1H, d, J=8.0 Hz), 7.90-7.94 (2H, m), 7.98-8.02 (1H, m), 8.09 (1H, s), 10.86 (1H, s).

B) (1r,4r)-4-((3,5-difluoropyridin-2-yl)oxy)-2'-oxo-1',2'-dihydrospiro[cyclohexane-1,3'-indole]-5'-carboxylic acid To a mixture of methyl (1r,4r)-4-((3,5-difluoropyridin-2-yl)oxy)-2'-oxo-1',2'-dihydrospiro[cyclohexane-1,3'-indole]-5'-carboxylate (500 mg), tetrahydrofuran (10 ml) and water (10 ml) was added lithium hydroxide monohydrate (216 mg) at room temperature, and the mixture was stirred under a nitrogen atmosphere at 50° C. for 3 hr and concentrated. To the residue was added 3N hydrochloric acid to adjust same to pH=3.0, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) to give the title compound (260 mg).

$^1$H NMR (400 MHz, CD$_3$OD) δ1.90-1.97 (4H, m), 2.10-2.12 (2H, m), 2.41-2.43 (2H, m), 5.35-5.41 (1H, m), 7.00-7.02 (1H, d, J=8.0 Hz), 7.55-7.59 (1H, m), 7.92 (1H, s), 7.93-8.01 (1H, m), 8.16 (1H, s).

Example 9

(1s,4s)-4-((3,5-dichloropyridin-2-yl)oxy)-2'-oxo-1',2'-dihydrospiro[cyclohexane-1,3'-indole]-5'-carboxylic Acid A) methyl (1s,4s)-4-hydroxy-2'-oxo-1',2'-dihydrospiro[cyclohexane-1,3'-indole]-5'-carboxylate To a mixture of methyl 2',4-dioxo-1',2'-dihydrospiro[cyclohexane-1,3'-indole]-5'-carboxylate (26 g) and tetrahydrofuran (300 ml) was added borane-tetrahydrofuran complex (1 mol/l tetrahydrofuran solution, 95 ml) at 0° C., and the mixture was stirred at the same temperature for 20 min. To the reaction mixture were added water at 0° C. and 1N hydrochloric acid (8 ml), and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (14.6 g).

$^1$H NMR (300 MHz, DMSO-$d_6$) δ 1.58-1.84 (6H, m), 1.86-2.06 (2H, m), 3.65-3.87 (4H, m), 4.60 (1H, d, J=3.9 Hz), 6.92 (1H, dd, J=8.6, 1.3 Hz), 7.73-7.90 (2H, m), 10.65 (1H, s). MS: [M–H]⁻ 274.0.

B) methyl (1s,4s)-4-((3,5-dichloropyridin-2-yl)oxy)-2'-oxo-1',2'-dihydrospiro[cyclohexane-1,3'-indole]-5'-carboxylate To a suspension of sodium hydride (60% in oil, 3.71 g) and tetrahydrofuran (200 ml) was added methyl (1s,4s)-4- hydroxy-2'-oxo-1',2'-dihydrospiro[cyclohexane-1,3'-indole]-5'-carboxylate (8.50 g) at 0° C., and the mixture was stirred at the same temperature for 30 min. After stirring, 3,5-dichloro-2-fluoropyridine (6.15 g) was added. After stirring at room temperature overnight, water was added to the reaction mixture and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (11.9 g).

MS: [M+H]$^+$ 421.1.

C) (1s,4s)-4-((3,5-dichloropyridin-2-yl)oxy)-2'-oxo-1',2'-dihydrospiro[cyclohexane-1,3'-indole]-5'-carboxylic Acid To a mixture of methyl (1s,4s)-4-((3,5-dichloropyridin-2-yl)oxy)-2'-oxo-1',2'-dihydrospiro[cyclohexane-1,3'-indole]-5'-carboxylate (100 g), methanol (500 ml) and tetrahydrofuran (500 ml) was added 2N aqueous sodium hydroxide solution (475 ml), and the mixture was stirred at 55° C. for 5 hr. To the reaction mixture was added 2N hydrochloric acid (475 ml) at room temperature, and the mixture was stirred at 15° C.-25° C. for 1 hr. The resulting precipitate was collected by filtration and washed with methanol/water (1:1, 200 ml) to give a white solid. The obtained solid was dissolved in dimethyl sulfoxide (300 ml) at 80° C., insoluble materials were removed by filtration, and dimethyl sulfoxide (60 ml) was added. Ethanol (630 ml) was added to the filtrate while maintaining at 50° C. and water (180 ml) was added at 50° C.–60° C. The mixture was stirred at the same temperature for 30 min. After stirring, the mixture was slowly cooled to room temperature, further ice-cooled and stirred. The mixture was filtered, and the filtrate was washed with ethanol-water (1:1, 200 ml) to give the title compound (80 g). The data of the crystal of the title compound is shown in Table 4 and the molecule structure obtained by single crystal X-ray structure analysis is shown in FIG. 1.

$^1$H NMR (300 MHz, DMSO-d$_6$) δ 1.78-2.09 (6H, m), 2.18-2.35 (2H, m), 5.28-5.40 (1H, m), 6.92 (1H, d, J=8.1 Hz), 7.84 (1H, d, J=8.1 Hz), 7.95 (1H, s), 8.15-8.26 (2H, m), 10.72 (1H, s), 12.64 (1H, brs). MS: [M−H]$^-$ 404.9. Anal. Calcd for c$_{19}$H$_{16}$N$_2$O$_4$Cl$_2$:C, 56.04; H, 3.96; N, 6.88. Found: C, 55.67; H, 4.12; N, 7.10. mp 302° C.

TABLE 4

| | |
|---|---|
| molecular formula | C$_{19}$H$_{16}$Cl$_2$N$_2$O$_4$ |
| molecular weight | 407.25 |
| color of crystal, crystal habit | colorless, plate |
| temperature (K) | 100 |
| crystal size (mm) | 0.151 × 0.122 × 0.068 |
| crystal system | monoclinic |
| space group | I2/a |
| lattice constant (Å, °) | a = 17.5416(4) |
| | b = 7.1049(3) |
| | c = 31.6985(9) |
| | α = γ = 90°, β = 90.346(2)° |
| volume (Å$^3$) | 3950.6(2) |
| Z | 8 |
| density (Calculated) (g/cm$^3$) | 1.369 |
| radiation | Cu-Kα (1.5419 Å) |
| absorption coefficient (mm$^{-1}$) | 0.319 |
| goodness of fit on F$^2$ | 1.060 |
| R$_1$ [I > 2σ(I)] | 0.055 |
| wR$_2$ (all data) | 0.168 |

Example 14

(1r,4r)-4-((3,5-dichloropyridin-2-yl)oxy)-2'-oxo-1',2'-dihydrospiro[cyclohexane-1,3'-indole]-5'-carboxylic Acid To a mixture of methyl (1r,4r)-4-hydroxy-2'-oxo-1',2'-dihydrospiro[cyclohexane-1,3'-indole]-5'-carboxylate (1.00 g) and tetrahydrofuran (60 ml) was added sodium hydride (60% in oil, 436 mg) at 0° C., and the mixture was stirred at the same temperature for 30 min and 3,5-dichloro-2-fluoropyridine (723 mg) was added. After stirring at room temperature for 8 hr, N,N-dimethylformamide (60 ml) was added, and the mixture was further stirred at room temperature for 12 hr. The reaction mixture was poured into ice-cooled water and extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) to give a white solid. To a mixture of the obtained solid, tetrahydrofuran (20 ml) and water (20 ml) was added lithium hydroxide monohydrate (130 mg) at room temperature, and the mixture was stirred at 50° C. for 3 hr and concentrated under reduced pressure. The residue was adjusted to pH=3.0 by adding 3N hydrochloric acid and extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) to give the title compound (1.00 g).

$^1$H NMR (400 MHz, MeOD) δ1.84-1.85 (2H, m), 2.03-2.11 (4H, m), 2.46-2.48 (2H, m), 5.43-5.44 (1H, m), 7.00-7.02 (1H, d, J=8.0 Hz), 7.92-7.93 (1H, d, J=2.4 Hz), 7.98-8.00 (1H, t, J=8.0, 1.2 Hz), 8.09-8.11 (1H, t, J=8.0, 1.2 Hz), 8.12 (1H, s).

Example 15

(1s,4s)-4-(2,4-dichlorophenoxy)-2'-oxo-1',2'-dihydrospiro[cyclohexane-1,3'-indole]-5'-carboxylic Acid A) methyl (1s,4s)-4-(2,4-dichlorophenoxy)-2'-oxo-1',2'-dihydrospiro[cyclohexane-1,3'-indole]-5'-carboxylate To a mixture of diisopropyl azodicarboxylate (1.9 mol/l toluene solution, 0.315 ml), triphenylphosphine (157 mg) and tetrahydrofuran (2 ml) was added 2,4-dichlorophenol (78 mg) at room temperature, a solution of methyl (1r,4r)-4-hydroxy-2'-oxo-1',2'-dihydrospiro[cyclohexane-1,3'-indole]-5'-carboxylate (110 mg) in tetrahydrofuran (2 ml) was added, and the mixture was stirred at room temperature overnight. Water was added to the reaction mixture and the mixture was extracted with ethyl acetate. The organic layer was separated, washed with saturated brine, dried over anhydrous magnesium sulfate and concentrated under reduced pressure. The residue was purified by silica gel column chromatography (ethyl acetate/hexane) to give the title compound (116 mg).

$^1$H NMR (400 MHz, DMSO-d$_6$) δ 1.81-1.99 (6H, m), 2.21 (2H, dd, J=12.9, 7.0 Hz), 3.82 (3H, s), 4.70-4.76 (1H, m), 6.95 (1H, d, J=8.2 Hz), 7.27-7.34 (1H, m), 7.34-7.45

(1H, m), 7.58 (1H, d, J=2.6 Hz), 7.83-7.92 (2H, m), 10.76 (1H, brs). MS: [M–H]⁻ 418.1.

B) (1s,4s)-4-(2,4-dichlorophenoxy)-2'-oxo-1',2'-dihydrospiro[cyclohexane-1,3'-indole]-5'-carboxylic acid A mixture of methyl (1s,4s)-4-(2,4-dichlorophenoxy)-2'-oxo-1',2'-dihydrospiro[cyclohexane-1,3'-indole]-5'-carboxylate (115 mg), 2N aqueous sodium hydroxide solution (1.35 ml), tetrahydrofuran (2 ml) and methanol (2 ml) was stirred at 50° C. overnight, concentrated under reduced pressure, and water and ethyl acetate were added to the residue. The aqueous layer was separated, neutralized with 6N hydrochloric acid, and extracted with ethyl acetate. The organic layer was separated, washed with water and saturated brine, dried over anhydrous magnesium sulfate and concentrated under reduced pressure. The residue was washed with diisopropyl ether to give the title compound (25.0 mg).
¹H NMR (400 MHz, DMSO-d₆) δ1.78-1.98 (6H, m), 2.20 (2H, d, J=9.5 Hz), 4.66-4.83 (1H, m), 6.92 (1H, d, J=8.0 Hz), 7.25-7.33 (1H, m), 7.34-7.43 (1H, m), 7.59 (1H, d, J=2.4 Hz), 7.84 (1H, d, J=8.2 Hz), 7.90 (1H, s), 10.70 (1H, s), 12.64 (1H, brs).

Example 16

(1r,4r)-4-((3-chloro-5-cyclopropylpyridin-2-yl)oxy)-2'-oxo-1',2'-dihydrospiro[cyclohexane-1,3'-pyrrolo[3,2-b]pyridine]-5'-carboxylic Acid

A) 3-chloro-5-cyclopropyl-2-methoxypyridine

To a mixture of cyclopropylboronic acid (1.26 g), 5-bromo-3-chloro-2-methoxypyridine (2.50 g), toluene (30 ml) and water (3 ml) were added palladium(II) acetate (126 mg), tricyclohexylphosphine (315 mg) and tripotassium phosphate (7.16 g), and the mixture was stirred under a nitrogen atmosphere at 100° C. overnight. Water was added to the mixture and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (1.20 g).
MS: [M+H]⁺ 184.3.

B) 3-chloro-5-cyclopropylpyridin-2-ol

To a solution of 3-chloro-5-cyclopropyl-2-methoxypyridine (2.10 g) in N,N-dimethylformamide (30 ml) was added pyridine hydrochloride (13.2 g) and the mixture was stirred at 100° C. for 2 hr. To the reaction mixture was added saturated brine, and the mixture was extracted with ethyl acetate. The organic layer was separated, washed twice with saturated brine, dried over anhydrous magnesium sulfate and concentrated under reduced pressure. The residue was washed with a hexane-toluene (1:1) mixed solution to give the title compound (820 mg).
MS: [M+H]⁺ 170.3.

C) methyl 5'-chloro-2',4-dioxo-1',2'-dihydrospiro[cyclohexane-1,3'-pyrrolo[3,2-b]pyridine]-3-carboxylate To a mixture of 5-chloro-1,3-dihydro-2H-pyrrolo[3,2-b]pyridin-2-one (23.0 g), potassium tert-butoxide (784 mg) and dimethyl sulfoxide (200 ml) was added dropwise methyl acrylate (37.2 ml) at 40° C. for 30 min under a nitrogen atmosphere, and the reaction mixture was slowly heated to 60° C. After stirring at the same temperature for 1 hr, potassium tert-butoxide (46.1 g) was added in 6 portions at 10 min intervals, and the mixture was stirred for 30 min. The reaction mixture was cooled to room temperature and diluted with ethyl acetate, and ice water was added. The organic layer was separated, washed with water and saturated brine, dried over anhydrous sodium sulfate, and concentrated under reduced pressure. The residue was purified by silica gel column chromatography (ethyl acetate/hexane) to give the title compound (13.7 g).
¹H NMR (400 MHz, DMSO-d₆) δ 1.84-1.94 (2H, m), 2.006-2.10 (1H, m), 2.34-2.72 (3H, m), 3.68 (3H, s), 7.27-7.32 (2H, m), 10.79 (1H, s), 12.15 (1H, s).

D) 5'-chloro-4H-spiro[cyclohexane-1,3'-pyrrolo[3,2-b]pyridine]-2',4(1'H)-dione To a mixture of methyl 5'-chloro-2',4-dioxo-1',2'-dihydrospiro[cyclohexane-1,3'-pyrrolo[3,2-b]pyridine]-3-carboxylate (13.7 g), dimethyl sulfoxide (140 ml) and water (11 ml) was added lithium chloride (9.45 g), and the mixture was stirred at 130° C. for 24 hr. Ice water was added to the reaction mixture at room temperature and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (10.2 g).
¹H NMR (400 MHz, DMSO-d₆) δ 2.03-2.09 (4H, m), 2.54-2.60 (2H, m), 2.69-2.76 (2H, m), 7.32-7.37 (2H, m), 10.86 (1H, s).

E) methyl 2',4-dioxo-1',2'-dihydrospiro[cyclohexane-1,3'-pyrrolo[3,2-b]pyridine]-5'-carboxylate To a mixture of 5'-chloro-4H-spiro[cyclohexane-1,3'-pyrrolo[3,2-b]pyridine]-2',4(1'H)-dione (5.50 g), methanol (50 ml) and N,N-dimethylformamide (50 ml) were added [1,1-bis(diphenylphosphino)ferrocene]dichloropalladium(II) (1.61 g) and triethylamine (6.12 ml), and the mixture was stirred under a carbon monoxide atmosphere (0.5 Mpa) at 100° C. for 6 hr. The reaction mixture was filtered through celite, and the filtrate was concentrated under reduced pressure to a half amount. The concentrate was poured into water, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (3.76 g).
MS: [M+H]⁺ 275.1.

F) methyl 5'-bromo-2',4-dioxo-1',2'-dihydrospiro[cyclohexane-1,3'-pyrrolo[3,2-b]pyridine]-3-carboxylate To a mixture of 5-bromo-1H-pyrrolo[3,2-b]pyridine-2(3H)-one (2 g) and dimethyl sulfoxide (20 ml) was added potassium tert-butoxide (0.068 g) at room temperature, and the mixture was stirred at the same temperature for 10 min. After stirring, methyl acrylate (2.64 ml) was added dropwise at 40° C.-45° C. over 1 hr. The reaction mixture was stirred at the same temperature for 2 hr, potassium tert-butoxide (3.16 g) was added at 45° C. over 30 min and the mixture was stirred at 70° C. for 2 hr. Ice water was added to the reaction mixture and the mixture was extracted with ethyl acetate. The organic layer was separated, dried over anhydrous sodium sulfate, and concentrated under reduced pressure. The residue was purified by silica gel column chromatography (ethyl acetate/petroleum ether) to give the title compound (1 g).
MS: [M+H]$^+$ 353.2.

G) 5'-bromo-4H-spiro[cyclohexane-1,3'-pyrrolo[3,2-b]pyridine]-2',4(1'H)-dione

To a mixture of methyl 5'-bromo-2',4-dioxo-1',2'-dihydrospiro[cyclohexane-1,3'-pyrrolo[3,2-b]pyridine]-3-carboxylate (24 g) and dimethyl sulfoxide (72 ml) was added an aqueous solution (72 ml) of sodium hydroxide (2.73 g) at room temperature, and the mixture was stirred at 130° C. for 2 hr. The reaction mixture was diluted with ethyl acetate and washed with water. The organic layer was separated, washed with saturated brine, dried over anhydrous sodium sulfate, and concentrated under reduced pressure. The residue was washed with n-pentane to give the title compound (14 g).
MS: [M+H]$^+$ 295.1.

H) methyl 2',4-dioxo-1',2'-dihydrospiro[cyclohexane-1,3'-pyrrolo[3,2-b]pyridine]-5'-carboxylate To a mixture of 5'-bromo-4H-spiro[cyclohexane-1,3'-pyrrolo[3,2-b]pyridine]-2',4(1'H)-dione (0.50 g), methanol (1 ml) and N,N-dimethylformamide (2.5 ml) was added triethylamine (0.47 ml) at room temperature, a deaeration operation was performed with argon, and 1,3-bis (diphenylphosphino)propane (0.139 g) and palladium(II) acetate (0.038 g) were added. The mixture was stirred under a carbon monoxide gas atmosphere (300 psi) at 100° C. for 24 hr, filtered through celite, and the filtrate was concentrated under reduced pressure. The residue was diluted with ethyl acetate, washed with water, dried over anhydrous sodium sulfate, and concentrated under reduced pressure. The residue was purified by silica gel column chromatography (ethyl acetate/hexane) to give the title compound (0.235 g).
MS: [M+H]$^+$ 275.2.

I) methyl (1r,4r)-4-hydroxy-2'-oxo-1',2'-dihydrospiro[cyclohexane-1,3'-pyrrolo[3,2-b]pyridine]-5'-carboxylate (I) and methyl (1s,4s)-4-hydroxy-2'-oxo-1',2'-dihydrospiro[cyclohexane-1,3'-pyrrolo[3,2-b]pyridine]-5'-carboxylate (II)

To a mixture of methyl 2',4-dioxo-1',2'-dihydrospiro[cyclohexane-1,3'-pyrrolo[3,2-b]pyridine]-5'-carboxylate (1.71 g) and tetrahydrofuran (50 ml) was added sodium borohydride (0.472 g) at 0° C., and the mixture was stirred at the same temperature for 30 min. To the reaction mixture was added 1N hydrochloric acid at 0° C., and the mixture was extracted with ethyl acetate. The organic layer was separated, washed with water and saturated brine, dried over anhydrous magnesium sulfate and concentrated under reduced pressure. The residue was purified by HPLC (column CHIRALPAKOJ (MC001), mobile phase: hexane/ethanol (70/30, v/v)) to give the title compound (I) (1.05 g) and the title compound (II) (0.57 g).
The Title Compound (I)
$^1$H NMR (300 MHz, DMSO-d$_6$) δ 1.50-1.67 (2H, m), 1.74-2.06 (6H, m), 3.72 (1H, d, J=3.3 Hz), 3.85 (3H, s), 4.67 (1H, d, J=2.8 Hz), 7.28 (1H, d, J=8.2 Hz), 7.94 (1H, d, J=8.2 Hz), 10.92 (1H, brs).

The Title Compound (II)
$^1$H NMR (300 MHz, DMSO-d$_6$) δ 1.52-1.71 (2H, m), 1.75-2.04 (6H, m), 3.75 (1H, d, J=2.8 Hz), 3.84 (3H, s), 4.59 (1H, d, J=3.7 Hz), 7.26 (1H, d, J=8.2 Hz), 7.92 (1H, d, J=8.2 Hz), 10.87 (1H, brs).

J) methyl (1r,4r)-4-((3-chloro-5-cyclopropylpyridin-2-yl)oxy)-2'-oxo-1',2'-dihydrospiro[cyclohexane-1,3'-pyrrolo[3,2-b]pyridine]-5'-carboxylate To a mixture of triphenylphosphine (285 mg), diisopropyl azodicarboxylate (1.9 mol/l toluene solution, 0.571 ml), 3-chloro-5-cyclopropylpyridin-2-ol (184 mg) and toluene (5 ml) was added methyl (1s,4s)-4-hydroxy-2'-oxo-1',2'-dihydrospiro[cyclohexane-1,3'-pyrrolo[3,2-b]pyridine]-5'-carboxylate (150 mg) at room temperature, and the mixture was stirred at the same temperature for 16 hr. To the reaction mixture was added a saturated aqueous sodium hydrogen carbonate solution at room temperature, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (38.4 mg).
MS: [M+H]$^+$ 428.1.

K) (1r,4r)-4-((3-chloro-5-cyclopropylpyridin-2-yl)oxy)-2'-oxo-1',2'-dihydrospiro[cyclohexane-1,3'-pyrrolo[3,2-b]pyridine]-5'-carboxylic Acid A mixture of methyl (1r,4r)-4-((3-chloro-5-cyclopropylpyridin-2-yl)oxy)-2'-oxo-1',2'-dihydrospiro[cyclohexane-1,3'-pyrrolo[3,2-b]pyridine]-5'-carboxylate (38.4 mg), 2N aqueous sodium hydroxide solution (0.135 ml), tetrahydrofuran (3 ml) and methanol (1 ml) was stirred at 50° C. for 5 hr and the reaction mixture was concentrated under reduced pressure. Water and ethyl acetate were added to the obtained residue, the aqueous layer was separated, neutralized with 6N hydrochloric acid and extracted with ethyl acetate. The organic layer was separated, washed with water and saturated brine, dried over anhydrous magnesium sulfate and concentrated under reduced pressure. The residue was purified by HPLC (L-Column 2 ODS, mobile phase: water/acetonitrile (containing 0.1% TFA)) to give the title compound (18.0 mg).
$^1$H NMR (300 MHz, CDCl$_3$) δ 0.56-0.69 (2H, m), 0.87-1.02 (2H, m), 1.75-1.95 (3H, m), 2.15-2.48 (6H, m), 5.39 (1H, d, J=2.9 Hz), 7.35 (1H, d, J=2.0 Hz), 7.40 (1H, d, J=8.2 Hz), 7.89 (1H, d, J=2.0 Hz), 8.17 (1H, d, J=8.2 Hz), 8.84 (1H, brs).

Example 29

(1r,4r)-4-((3-chloro-5-(trifluoromethyl)pyridin-2-yl)oxy)-2'-oxo-1',2'-dihydrospiro[cyclohexane-1,3'-indole]-5'-carboxylic Acid To a mixture of diisopropyl azodicarboxylate (1.9 mol/l toluene solution, 0.031 ml), 3-chloro-2-hydroxy-5-(trifluoromethyl)pyridine (31.6 mg) and toluene (0.5 ml) was added a suspension of methyl (1s,4s)-4-hydroxy-2'-oxospiro[cyclohexane-1,3'-indoline]-5'-carboxylate (0.028 g) in toluene (0.5 ml) at 80° C., and the mixture was stirred at the same temperature for 3 hr. The reaction mixture was diluted with ethyl acetate and the reaction was discontinued with water. The organic layer was separated and concentrated by blowing air at 60° C. The residue was purified by HPLC (Actus Triart C18, mobile phase: water/acetonitrile (10 mM ammonium bicarbonate)). The obtained fraction was concentrated by blowing air at 60° C. To a mixture of the residue, tetrahydrofuran (0.3 ml) and methanol (0.3 ml) was added 2N sodium hydroxide (0.50 ml), and the mixture was stirred at 50° C. for 3 hr. The mixture was m neutralized with 6N hydrochloric acid and purified by HPLC (Actus Triart C18, mobile phase: water/acetonitrile (10 mM ammonium bicarbonate)) to give the title compound (12.1 mg).

Example 81

(1s,4s)-4-((5-chloro-3-methylpyridin-2-yl)oxy)-2'-oxo-1',2'-dihydrospiro[cyclohexane-1,3'-pyrrolo[3,2-b]pyridine]-5'-carboxylic Acid A) methyl (1s,4s)-4-((5-chloro-3-methylpyridin-2-yl)oxy)-2'-oxo-1',2'-dihydrospiro[cyclohexane-1,3'-pyrrolo[3,2-b]pyridine]-5'-carboxylate To a mixture of triphenylphosphine (285 mg), diisopropyl azodicarboxylate (1.9 mol/l toluene solution, 0.571 ml) and toluene (5 ml) was added 5-chloro-3-methylpyridin-2-ol (156 mg) at room temperature, methyl (1r,4r)-4-hydroxy-2'-oxo-1',2'-dihydrospiro[cyclohexane-1,3'-pyrrolo[3,2-b]pyridine]-5'-carboxylate (150 mg) was added, and the mixture was stirred at the same temperature for 16 hr. A saturated aqueous sodium hydrogen carbonate solution was added to the mixture at room temperature, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (289 mg) as a crude purified product.
MS: [M+H]$^+$ 402.1.

B) (1s,4s)-4-((5-chloro-3-methylpyridin-2-yl)oxy)-2'-oxo-1',2'-dihydrospiro[cyclohexane-1,3'-pyrrolo[3,2-b]pyridine]-5'-carboxylic Acid A mixture of methyl (1s,4s)-4-((5-chloro-3-methylpyridin-2-yl)oxy)-2'-oxo-1',2'-dihydrospiro[cyclohexane-1,3'-pyrrolo[3,2-b]pyridine]-5'-carboxylate (289 mg), 2N aqueous sodium hydroxide solution (3.60 ml), tetrahydrofuran (4 ml) and methanol (4 ml) was stirred at 50° C. for 1 hr, and the reaction mixture was concentrated under reduced pressure. Water and ethyl acetate were added to the residue, and the aqueous layer was separated and neutralized with 6N hydrochloric acid. The mixture was extracted with ethyl acetate. The organic layer was separated, washed with water and saturated brine, dried over anhydrous magnesium sulfate and concentrated under reduced pressure. The residue was purified by HPLC (L-Column 2 ODS, mobile phase: water/acetonitrile (containing 0.1% TFA)) to give the title compound (36.9 mg).
$^1$H NMR (300 MHz, DMSO-d$_6$) 51.69 (2H, brs), 2.04 (4H, brs), 2.23 (3H, brs), 2.36 (2H, brs), 5.32 (1H, brs), 7.31 (1H, brs), 7.71 (1H, brs), 7.87-8.19 (2H, m), 10.96 (1H, brs), 12.73 (1H, brs).

Example 83

(1s,4s)-4-(4-chloro-2-methoxyphenoxy)-2'-oxo-1',2'-dihydrospiro[cyclohexane-1,3'-indole]-5'-carboxylic Acid To a mixture of diisopropyl azodicarboxylate (1.9 mol/l toluene solution, 0.612 ml), triphenylphosphine (305 mg) and tetrahydrofuran (10 ml) were added 4-chloro-2-methoxyphenol (184 mg) and methyl (1r,4r)-4-hydroxy-2'-oxo-1',2'-dihydrospiro[cyclohexane-1,3'-indole]-5'-carboxylate (160 mg) at room temperature, and the mixture was stirred at the same temperature for 16 hr. To the mixture was added a saturated aqueous sodium hydrogen carbonate solution at room temperature, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane), and the obtained solid was washed with diisopropylether-ethyl acetate to give a white solid. A mixture of the obtained solid, 2N sodium hydroxide (3.46 ml), tetrahydrofuran (4 ml) and methanol (4 ml) was stirred at 50° C. for 3 hr and concentrated under reduced pressure. Water and ethyl acetate were added to the residue, m and the aqueous layer was separated, neutralized with 6N hydrochloric acid and extracted with ethyl acetate. The organic layer was separated, washed with water and saturated brine, dried over anhydrous magnesium sulfate and concentrated under reduced pressure. The residue was purified by HPLC (L-Column 2 ODS, mobile phase: water/acetonitrile (containing 0.1% TFA)) to give the title compound (22.5 mg).
$^1$H NMR (300 MHz, DMSO-d$_6$) δ 1.69-1.98 (6H, m), 2.07-2.30 (2H, m), 3.80 (3H, s), 4.39-4.72 (1H, m), 6.86-6.96 (2H, m), 7.00-7.13 (2H, m), 7.83 (1H, d, J=8.2 Hz), 7.88 (1H, s), 10.68 (1H, s), 12.62 (1H, brs).

Example 87

(1s,4s)-4-((5-chloro-3-fluoropyridin-2-yl)oxy)-2'-oxo-1',2'-dihydrospiro[cyclohexane-1,3'-indole]-5'-carboxylic Acid A) methyl (1s,4s)-4-((5-chloro-3-fluoropyridin-2-yl)oxy)-2'-oxo-1',2'-dihydrospiro[cyclohexane-1,3'-indole]-5'-carboxylate To a suspension of sodium hydride (60% in oil, 65.4 mg) and tetrahydrofuran (5 ml) was added methyl (1s,4s)-4-hydroxy-2'-oxo-1',2'-dihydrospiro[cyclohexane-1,3'-indole]-5'-carboxylate (150 mg) at 0° C., and the mixture was stirred at the same temperature for 30 min. After stirring, 5-chloro-2,3-difluoropyridine (98 mg) was added. After stirring at room temperature overnight, to the mixture was added saturated aqueous ammonium chloride solution at 0° C., and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (189 mg).
MS: [M+H]$^+$ 405.1.

B) (1s,4s)-4-((5-chloro-3-fluoropyridin-2-yl)oxy)-2'-oxo-1',2'-dihydrospiro[cyclohexane-1,3'-indole]-5'-carboxylic Acid A mixture of methyl (1s,4s)-4-((5-chloro-3-fluoropyridin-2-yl)oxy)-2'-oxo-1',2'-dihydrospiro[cyclohexane-1,3'-indole]-5'-carboxylate (189 mg), 2N aqueous sodium hydroxide solution (2.33 ml), tetrahydrofuran (4 ml) and methanol (4 ml) was stirred at 50° C. for 3 hr and concentrated under reduced pressure. To the residue were added water and ethyl acetate. The aqueous layer was separated, neutralized with 6N hydrochloric acid and extracted with ethyl acetate. The organic layer was separated, washed with water and saturated brine, dried over anhydrous magnesium sulfate and concentrated under reduced pressure. The obtained solid was washed with diethylether-hexane to give the title compound (101 mg).

$^1$H NMR (300 MHz, DMSO-d$_6$) δ 1.71-2.09 (6H, m), 2.18-2.37 (2H, m), 5.24-5.44 (1H, m), 6.92 (1H, d, J=8.1 Hz), 7.84 (1H, d, J=8.3 Hz), 7.94 (1H, s), 8.03 (1H, dd, J=10.1, 2.0 Hz), 8.09 (1H, d, J=2.0 Hz), 10.70 (1H, s), 12.61 (1H, brs).

Example 97

(1s,4s)-4-((3,5-dichloropyridin-2-yl)oxy)-2'-oxo-1', 2'-dihydrospiro[cyclohexane-1,3'-pyrrolo[3,2-b]pyridine]-5'-carboxylic Acid A) methyl (1r,4r)-4-hydroxy-2'-oxo-1',2'-dihydrospiro[cyclohexane-1,3'-pyrrolo[3,2-b]pyridine]-5'-carboxylate To a mixture of lithium tri-sec-butylborohydride (1.02 M tetrahydrofuran solution, 7.15 ml) and tetrahydrofuran (20 ml) was added a solution of methyl 2',4-dioxo-1',2'-dihydrospiro[cyclohexane-1,3'-pyrrolo[3,2-b]pyridine]-5'-carboxylate (1.0 g) in tetrahydrofuran (20 ml) at −60° C. to −70° C. The reaction mixture was stirred at −70° C. for 1 hr, saturated aqueous ammonium chloride solution and saturated brine were added at −70° C., and the mixture was extracted with ethyl acetate. The organic layer was separated, washed with water and saturated brine, dried over anhydrous magnesium sulfate and concentrated under reduced pressure. The residue was washed with ethanol-diethyl ether to give the title compound (740 mg).

$^1$H NMR (300 MHz, DMSO-d$_6$) δ 1.49-1.72 (2H, m), 1.73-2.09 (6H, m), 3.64-3.77 (1H, m), 3.86 (3H, s), 4.67 (1H, d, J=2.8 Hz), 7.22-7.34 (1H, m), 7.87-7.99 (1H, m), 10.45-11.30 (1H, m). MS: [M+H]$^+$ 277.3.

B) 1'-tert-butyl 5'-methyl (1r,4r)-4-hydroxy-2'-oxospiro[cyclohexane-1,3'-pyrrolo[3,2-b]pyridine]-1',5' (2'H)-dicarboxylate A mixture of di-tert-butyl dicarbonate (9.66 g), sodium hydrogen carbonate (4.96 g), methyl (1r,4r)-4-hydroxy-2'-oxo-1',2'-dihydrospiro[cyclohexane-1,3'-pyrrolo[3,2-b]pyridine]-5'-carboxylate (8.15 g) and tetrahydrofuran (300 ml) was stirred at room temperature for 24 hr, tetrahydrofuran (200 ml) was added and the mixture was further stirred for 16 hr. The reaction mixture was concentrated under reduced pressure, water was added and the mixture was extracted with ethyl acetate. The organic layer was separated, washed with water and saturated brine, dried over anhydrous magnesium sulfate and concentrated under reduced pressure. The residue was washed with hexane to give the title compound (10.2 g).

MS: [M+H]$^+$ 377.3.

C) 1'-tert-butyl 5'-methyl (1s,4s)-4-((3,5-dichloro-pyridin-2-yl)oxy)-2'-oxospiro[cyclohexane-1,3'-pyrrolo[3,2-b]pyridine]-1',5'(2'H)-dicarboxylate A solution of diethyl azodicarboxylate (5.49 ml) in tetrahydrofuran (10 ml) was added to a suspension of 1'-tert-butyl 5'-methyl (1r,4r)-4-hydroxy-2'-oxospiro[cyclohexane-1,3'-pyrrolo[3,2-b]pyridine]-1',5'(2'H)-dicarboxylate (8.70 g), 3,5-dichloropyridin-2-ol (5.69 g), triphenylphosphine (9.09 g) in tetrahydrofuran (150 ml) at 0° C., and the mixture was stirred at room temperature for 4 hr. Water was added to the reaction mixture and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane), and the obtained solid was washed with hexane to give the title compound (7.80 g).

MS: [M+H]$^+$ 522.2.

D) methyl (1s,4s)-4-((3,5-dichloropyridin-2-yl)oxy)-2'-oxo-1',2'-dihydrospiro[cyclohexane-1,3'-pyrrolo [3,2-b]pyridine]-5'-carboxylate A mixture of 1'-tert-butyl 5'-methyl (1s,4s)-4-((3,5-dichloropyridin-2-yl)oxy)-2'-oxospiro[cyclohexane-1,3'-pyrrolo[3,2-b]pyridine]-1',5'(2'H)-dicarboxylate (10.3 g) and 10% hydrochloric acid methanol solution (500 ml) was stirred at 50° C. for 16 hr and concentrated under reduced pressure. To the residue was added saturated aqueous sodium hydrogen carbonate solution and the mixture was extracted with ethyl acetate-tetrahydrofuran. The organic layer was separated, washed with saturated brine, dried over anhydrous magnesium sulfate and concentrated under reduced pressure. The residue was washed with hexane to give the title compound (8.26 g).

$^1$H NMR (300 MHz, DMSO-d$_6$) δ 1.61-1.84 (2H, m), 1.94-2.21 (4H, m), 2.25-2.40 (2H, m), 3.86 (3H, s), 5.27-5.44 (1H, m), 7.31 (1H, d, J=8.2 Hz), 7.90-8.01 (1H, m), 8.17-8.20 (1H, m), 8.21-8.29 (1H, m), 10.91-11.06 (1H, m).

E) (1s,4s)-4-((3,5-dichloropyridin-2-yl)oxy)-2'-oxo-1',2'-dihydrospiro[cyclohexane-1,3'-pyrrolo[3,2-b] pyridine]-5'-carboxylic Acid A mixture of methyl (1s,4s)-4-((3,5-dichloropyridin-2-yl)oxy)-2'-oxo-1',2'-dihydrospiro[cyclohexane-1,3'-pyrrolo[3, 2-b]pyridine]-5'-carboxylate (14.8 g), 1N aqueous sodium hydroxide solution (150 ml), methanol (150 ml) and tetrahydrofuran (150 ml) was stirred at 60° C. for 5 hr, 1N hydrochloric acid (150 ml) and water were added and the mixture was stirred at room temperature for 1 hr. The resulting precipitate was collected by filtration and the obtained solid was crystallized from ethanol/water to give the title compound (12.7 g).

$^1$H NMR (300 MHz, DMSO-d$_6$) δ 1.61-1.82 (2H, m), 1.94-2.20 (4H, m), 2.27-2.46 (2H, m), 5.35 (1H, d, J=3.2 Hz), 7.31 (1H, s), 7.95 (1H, d, J=8.2 Hz), 8.17-8.20 (1H, m), 8.21-8.25 (1H, m), 10.68-11.32 (1H, m), 12.31-13.10 (1H, m). MS: [M−H]$^-$ 405.9. Anal. Calcd for c$_{18}$H$_{15}$C$_{12}$N$_3$O$_4$, C; 52.96. H; 3.70, N; 10.29. Found. C; 52.97, H; 3.62, N; 10.31. mp 282-283° C.

Example 98

(1r,4r)-4-((3,5-dichloropyridin-2-yl)oxy)-2'-oxo-1', 2'-dihydrospiro[cyclohexane-1,3'-pyrrolo[3,2-b]pyridine]-5'-carboxylic Acid A) methyl (1r,4r)-4-((3,5-dichloropyridin-2-yl)oxy)-2'-oxo-1',2'-dihydrospiro[cyclohexane-1,3'-pyrrolo [3,2-b]pyridine]-5'-carboxylate A solution of diisopropyl azodicarboxylate (1.65 g), triphenylphosphine (2.14 g), 3,5-dichloropyridin-2-ol (908 mg) and methyl (1s,4s)-4-hydroxy-2'-oxo-1',2'-dihydrospiro[cyclohexane-1,3'-pyrrolo[3,2-b]pyridine]-5'-carboxylate (901 mg) in tetrahydrofuran (10 ml) was stirred at 45° C. for 48 hr. The reaction mixture was concentrated under reduced pressure and methanol (5 ml) was added to the residue. The resulting precipitate was collected by filtration to give the title compound (470 mg).

MS: [M+H]$^+$ 422.1.

B) (1r,4r)-4-((3,5-dichloropyridin-2-yl)oxy)-2'-oxo-1',2'-dihydrospiro[cyclohexane-1,3'-pyrrolo[3,2-b]pyridine]-5'-carboxylic Acid To a solution of methyl (1r,4r)-4-((3,5-dichloropyridin-2-yl)oxy)-2'-oxo-1',2'-dihydrospiro[cyclohexane-1,3'-pyrrolo[3,2-b]pyridine]-5'-carboxylate (300 mg) in water (5 ml)/tetrahydrofuran (5 ml) was added lithium hydroxide monohydrate (149 mg) at room temperature, and the mixture was stirred at the same temperature for 24 hr. The mixture was adjusted with 1N hydrochloric acid to pH=4 and the resulting precipitate was collected by filtration. The obtained precipitate was purified by HPLC (Boston Green ODS, mobile phase: water (containing 0.225% formic acid)/acetonitrile) to give the title compound (146 mg).

$^1$H NMR (400 MHz, DMSO-$d_6$) δ 1.70-1.79 (2H, m), 1.79-2.00 (2H, m), 2.10-2.21 (2H, m), 2.21-2.45 (2H, m), 5.15-5.25 (1H, m), 7.30 (1H, d, J=8.0 Hz), 7.95 (1H, d, J=8.0 Hz), 8.19 (1H, d, J=2.4 Hz), 8.24 (1H, d, J=2.4 Hz), 10.99 (1H, s), 12.83 (1H, brs).

Example 101

(1s,4s)-4-(2,4-dichlorophenoxy)-2'-oxo-1',2'-dihydrospiro[cyclohexane-1,3'-pyrrolo[3,2-b]pyridine]-5'-carboxylic Acid A) methyl (1s,4s)-4-(2,4-dichlorophenoxy)-2'-oxo-1',2'-dihydrospiro[cyclohexane-1,3'-pyrrolo[3,2-b]pyridine]-5'-carboxylate To a solution of methyl (1r,4r)-4-hydroxy-2'-oxo-1',2'-dihydrospiro[cyclohexane-1,3'-pyrrolo[3,2-b]pyridine]-5'-carboxylate (40 mg) and 2,4-dichlorophenol (28.3 mg) in tetrahydrofuran (5 ml) were added triphenylphosphine (45.6 mg) and diisopropyl azodicarboxylate (1.9 mol/l toluene solution, 0.114 ml), and the mixture was stirred at room temperature overnight. The reaction mixture was poured into water and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (21 mg).

MS: [M+H]$^+$ 421.1.

B) (1s,4s)-4-(2,4-dichlorophenoxy)-2'-oxo-1',2'-dihydrospiro[cyclohexane-1,3'-pyrrolo[3,2-b]pyridine]-5'-carboxylic Acid To a mixture of methyl (1s,4s)-4-(2,4-dichlorophenoxy)-2'-oxo-1',2'-dihydrospiro[cyclohexane-1,3'-pyrrolo[3,2-b]pyridine]-5'-carboxylate (21 mg), methanol (2 ml) and tetrahydrofuran (2 ml) was added 1N aqueous sodium hydroxide solution (1 ml), and the mixture was stirred at room temperature overnight. The reaction mixture was neutralized with 1N hydrochloric acid and the resulting white solid was collected by filtration and washed with ethanol-water to give the title compound (19 mg).

$^1$H NMR (300 MHz, DMSO-$d_6$) δ 1.70 (2H, d, J=5.3 Hz), 1.96-2.14 (4H, m), 2.30 (2H, d, J=17.6 Hz), 4.84 (1H, brs), 7.27 (1H, d, J=8.3 Hz), 7.36 (2H, s), 7.59 (1H, s), 7.92 (1H, d, J=8.1 Hz), 10.92 (1H, s), 12.80 (1H, brs).

Example 102

(1r,4r)-4-(2,4-dichlorophenoxy)-2'-oxo-1',2'-dihydrospiro[cyclohexane-1,3'-pyrrolo[3,2-b]pyridine]-5'-carboxylic Acid A) methyl (1r,4r)-4-(2,4-dichlorophenoxy)-2'-oxo-1',2'-dihydrospiro[cyclohexane-1,3'-pyrrolo[3,2-b]pyridine]-5'-carboxylate To a mixture of methyl (1s,4s)-4-hydroxy-2'-oxo-1',2'-dihydrospiro[cyclohexane-1,3'-pyrrolo[3,2-b]pyridine]-5'-carboxylate (40 mg), 2,4-dichlorophenol (28.3 mg) and tetrahydrofuran (5 ml) were added diisopropyl azodicarboxylate (1.9 mol/1 toluene solution, 0.152 ml) and triphenylphosphine (57.0 mg), and the mixture was stirred at room temperature overnight. The reaction mixture was poured into water, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give the title compound (40 mg).

MS: [M+H]$^+$ 421.1.

B) (1r,4r)-4-(2,4-dichlorophenoxy)-2'-oxo-1',2'-dihydrospiro[cyclohexane-1,3'-pyrrolo[3,2-b]pyridine]-5'-carboxylic Acid To a mixture of methyl (1r,4r)-4-(2,4-dichlorophenoxy)-2'-oxo-1',2'-dihydrospiro[cyclohexane-1,3'-pyrrolo[3,2-b]pyridine]-5'-carboxylate (21 mg), tetrahydrofuran (1 ml) and methanol (1 ml) was added 1N aqueous sodium hydroxide solution (0.5 ml), and the mixture was stirred at room temperature overnight. The reaction mixture was neutralized with 1N hydrochloric acid, the resulting white solid was collected by filtration and washed with water-ethanol to give the title compound (20 mg).

$^1$H NMR (300 MHz, DMSO-$d_6$) δ 1.66-1.97 (4H, m), 2.14 (2H, brs), 2.21-2.37 (2H, m), 4.64 (1H, brs), 7.29 (1H, d, J=8.1 Hz), 7.36 (2H, s), 7.58 (1H, s), 7.94 (1H, d, J=8.3 Hz), 10.95 (1H, s), 12.76 (1H, brs).

Example 115

(1s,4s)-4-((3-chloro-5-(trifluoromethyl)pyridin-2-yl)oxy)-2'-oxo-1',2'-dihydrospiro[cyclohexane-1,3'-pyrrolo[3,2-b]pyridine]-5'-carboxylic Acid To a mixture of triphenylphosphine (285 mg), diisopropyl azodicarboxylate (1.9 mol/l toluene solution, 0.571 ml) and toluene (5 ml) was added 3-chloro-5-(trifluoromethyl)pyridin-2-ol (214 mg) and methyl (1r,4r)-4-hydroxy-2'-oxo-1',2'-dihydrospiro[cyclohexane-1,3'-pyrrolo[3,2-b]pyridine]-5'-carboxylate (150 mg) at room temperature, and the mixture was stirred at the same temperature for 16 hr. To the reaction mixture was added saturated aqueous sodium hydrogen carbonate solution at room temperature, and the mixture was extracted with ethyl acetate. The organic layer was separated, washed with water and saturated brine, dried over anhydrous magnesium sulfate and concentrated under reduced pressure. The residue was purified by silica gel column chromatography (ethyl acetate/hexane) to give a pale-yellow oil. A mixture of the obtained oil, 2N aqueous sodium hydroxide solution (4.01 ml), tetrahydrofuran (4 ml) and methanol (4 ml) was stirred at 50° C. for 3 hr and the reaction mixture was concentrated under reduced pressure. Water and ethyl acetate were added to the obtained residue, the aqueous layer was separated and neutralized with 6N hydrochloric acid and extracted with ethyl acetate. The organic layer was separated, washed with water and saturated brine, dried over anhydrous magnesium sulfate and concentrated under reduced pressure. The residue was purified by HPLC (L-Column 2 ODS, mobile phase: water/acetonitrile (containing 0.1% TFA)) to give the title compound (30.6 mg).

$^1$H NMR (300 MHz, DMSO-$d_6$) δ 1.61-1.90 (2H, m), 1.92-2.22 (4H, m). 2.25-2.47 (2H, m), 5.50 (1H, brs), 7.31 (1H, d, J=8.2 Hz), 7.95 (1H, d, J=8.2 Hz), 8.41 (1H, s), 8.58 (1H, s), 10.97 (1H, s), 12.73 (1H, brs).

Example compounds are shown in the following Table 5. In Tables, MS shows measured values. The compounds of Examples 2, 5-8, 10-13, 17-28, 30-80, 82, 84-86, 88-96, 99, 100, 103-114 in the following Table were produced according to the methods shown in the above-mentioned Examples or a method analogous thereto.

TABLE 5-1

| Ex. No. | IUPAC name | structural formula | MS |
|---|---|---|---|
| 1 | (1r,4r)-4-(2,4-dichlorophenoxy)-2'-oxo-1',2'-dihydrospiro[cyclohexane-1,3'-indole]-5'-carboxylic acid | | 404 |
| 2 | (1r,4r)-4-(4-fluorophenoxy)-2'-oxo-1',2'-dihydrospiro[cyclohexane-1,3'-indole-5'-carboxylic acid | | 353.9 |
| 3 | (1r,4r)-2'-oxo-4-(2,4,6-trichlorophenoxy)-1',2'-dihydrospiro[cyclohexane-1,3'-indole]-5'-carboxylic acid | | 437.9 |
| 4 | (1r,4r)-4-((3,5-difluoropyridin-2-yl)oxy)-2'-oxo-1',2'-dihydrospiro[cyclohexane-1,3'-indole]-5'-carboxylic acid | | 373 |

TABLE 5-2

| Ex. No. | IUPAC name | structural formula | MS |
|---|---|---|---|
| 5 | (1s,4s)-4-((2,5-difluoropyridin-3-yl)oxy)-2'-oxo-1',2'-dihydrospiro[cyclohexane-1,3'-indole]-5'-carboxylic acid | | 373 |
| 6 | (1r,4r)-2'-oxo-4-((6-(trifluoromethyl)pyridin-3-yl)oxy)-1',2'-dihydrospiro[cyclohexane-1,3'-indole]-5'-carboxylic acid | | 405 |
| 7 | (1r,4r)-4-(4-chloro-2-cyanophenoxy)-2'-oxo-1',2'-dihydrospiro[cyclohexane-1,3'-indole]-5'-carboxylic acid | | 397.1 |
| 8 | (1r,4r)-4-(2-carbamoyl-4-chlorophenoxy)-2'-oxo-1',2'-dihydrospiro[cyclohexane-1,3'-indole]-5'-carboxylic acid | | 413.1 |

TABLE 5-2-continued

| Ex. No. | IUPAC name | structural formula | MS |
|---|---|---|---|
| 9 | (1s,4s)-4-((3,5-dichloropyridin-2-yl)oxy)-2'-oxo-1',2'-dihydrospiro[cyclohexane-1,3'-indole]-5'-carboxylic acid | | 404.9 |

TABLE 5-3

| Ex. No. | IUPAC name | structural formula | MS |
|---|---|---|---|
| 10 | (1r,4r)-2'-oxo-4-(4-(trifluoromethyl)phenoxy)-1',2'-dihydrospiro[cyclohexane-1,3'-indole]-5'-carboxylic acid | | 404.1 |
| 11 | (1r,4r)-4-((5-chloropyridin-2-yl)oxy)-2'-oxo-1',2'-dihydrospiro[cyclohexane-1,3'-indole]-5'-carboxylic acid | | 371 |
| 12 | (1r,4r)-4-(2-chlorophenoxy)-2'-oxo-1',2'-dihydrospiro[cyclohexane-1,3'-indole]-5'-carboxylic acid | | 370.1 |

TABLE 5-3-continued

| Ex. No. | IUPAC name | structural formula | MS |
|---|---|---|---|
| 13 | (1s,4s)-4-((3,5-difluoropyridin-2-yl)oxy)-2'-oxo-1',2'-dihydrospiro[cyclohexane-1,3'-indole]-5'-carboxylic acid | | 375.1 |
| 14 | (1r,4r)-4-((3,5-dichloropyridin-2-yl)oxy)-2'-oxo-1',2'-dihydrospiro[cyclohexane-1,3'-indole]-5'-carboxylic acid | | 404.9 |

TABLE 5-4

| Ex. No. | IUPAC name | structural formula | MS |
|---|---|---|---|
| 15 | (1s,4s)-4-(2,4-dichlorophenoxy)-2'-oxo-1',2'-dihydrospiro[cyclohexane-1,3'-indole]-5'-carboxylic acid | | 404 |
| 16 | (1r,4r)-4-((3-chloro-5-cyclopropylpyridin-2-yl)oxy)-2'-oxo-1',2'-dihydrospiro[cyclohexane-1,3'-pyrrolo[3,2-b]pyridine]-5'-carboxylic acid | | 414.1 |

TABLE 5-4-continued

| Ex. No. | IUPAC name | structural formula | MS |
|---|---|---|---|
| 17 | (1r,4r)-4-((5-chloro-3-methylpyridin-2-yl)oxy)-2'-oxo-1',2'-dihydrospiro[cyclohexane-1,3'-pyrrolo[3,2-b]pyridine]-5'-carboxylic acid | | 386 |
| 18 | (1r,4r)-4-((6-methyl-3-(trifluoromethyl)pyridin-2-yl)oxy)-2'-oxo-1',2'-dihydrospiro[cyclohexane-1,3'-pyrrolo[3,2-b]pyridine]-5'-carboxylic acid | | 420.1 |
| 19 | (1r,4r)-2'-oxo-4-[pyridin-2-yloxy)-1',2'-dihydrospiro[cyclohexane-1,3'-indole]-5'-carboxylic acid | | 337 |

TABLE 5-5

| Ex. No. | IUPAC name | structural formula | MS |
|---|---|---|---|
| 20 | (1r,4r)-4-((5-methylpyridin-2-yl)oxy)-2'-oxo-1',2'-dihydrospiro[cyclohexane-1,3'-indole]-5'-carboxylic acid | | 353.1 |

TABLE 5-5-continued

| Ex. No. | IUPAC name | structural formula | MS |
|---|---|---|---|
| 21 | (1r,4r)-4-((3-methylpyridin-2-yl)oxy)-2'-oxo-1',2'-dihydrospiro[cyclohexane-1,3'-indole]-5'-carboxylic acid | | 351.1 |
| 22 | (1r,4r)-4-((5-fluoropyridin-2-yl)oxy)-2'-oxo-1',2'-dihydrospiro[cyclohexane-1,3'-indole]-5'-carboxylic acid | | 355.1 |
| 23 | (1r,4r)-4-((4-chloropyridin-2-yl)oxy)-2'-oxo-1',2'-dihydrospiro[cyclohexane-1,3'-indole]-5'-carboxylic acid | | 371.4 |
| 24 | (1r,4r)-4-((3-chloropyridin-2-yl)oxy)-2'-oxo-1',2'-dihydrospiro[cyclohexane-1,3'-indole]-5'-carboxylic acid | | 371.1 |

TABLE 5-6

| Ex. No. | IUPAC name | structural formula | MS |
|---|---|---|---|
| 25 | (1r,4r)-2'-oxo-4-((5-(trifluoromethyl)pyridin-2-yl)oxy)-1',2'-dihydrospiro[cyclohexane-1,3'-indole]-5'-carboxylic acid | | 405.1 |
| 26 | (1r,4r)-4-((6-methyl-3-(trifluoromethyl)pyridin-2-yl)oxy)-2'-oxo-1',2'-dihydrospiro[cyclohexane-1,3'-indole]-5'-carboxylic acid | | 419.1 |
| 27 | (1r,4r)-4-((3-fluoro-5-(trifluoromethyl)pyridin-2-yl)oxy)-2'-oxo-1',2'-dihydrospiro[cyclohexane-1,3'-indole]-5'-carboxylic acid | | 423.1 |
| 28 | (1r,4r)-4-((5-chloro-3-(trifluoromethyl)pyridin-2-yl)oxy)-2'-oxo-1',2'-dihydrospiro[cyclohexane-1,3'-indole]-5'-carboxylic acid | | 439.1 |

TABLE 5-6-continued

| Ex. No. | IUPAC name | structural formula | MS |
|---|---|---|---|
| 29 | (1r,4r)-4-((3-chloro-5-(trifluoromethyl)pyridin-2-yl)oxy)-2'-oxo-1',2'-dihydrospiro[cyclohexane-1,3'-indole]-5'-carboxylic acid | | 439.1 |

TABLE 5-7

| Ex. No. | IUPAC name | structural formula | MS |
|---|---|---|---|
| 30 | (1r,4r)-4-((4-(benzyloxy)pyridin-2-yl)oxy)-2'-oxo-1',2'-dihydrospiro[cyclohexane-1,3'-indole]-5'-carboxylic acid | | 445.2 |
| 31 | (1r,4r)-4-((5-cyclopropyl-3-(trifluoromethyl)pyridin-2-yl)oxy)-2'-oxo-1',2'-dihydrospiro[cyclohexane-1,3'-indole]-5'-carboxylic acid | | 445.1 |

TABLE 5-7-continued

| Ex. No. | IUPAC name | structural formula | MS |
|---|---|---|---|
| 32 | (1r,4r)-4-((2-methylpyridin-3-yl)oxy)-2'-oxo-1',2'-dihydrospiro[cyclohexane-1,3'-indole]-5'-carboxylic acid | | 353.1 |
| 33 | (1r,4r)-4-((5-methylpyridin-3-yl)oxy)-2'-oxo-1',2'-dihydrospiro[cyclohexane-1,3'-indole]-5'-carboxylic acid | | 353.1 |
| 34 | (1r,4r)-4-((6-methylpyridin-3-yl)oxy)-2'-oxo-1',2'-dihydrospiro[cyclohexane-1,3'-indole]-5'-carboxylic acid | | 353.1 |

TABLE 5-8

| Ex. No. | IUPAC name | structural formula | MS |
|---|---|---|---|
| 35 | (1r,4r)-4-((2,6-dimethylpyridin-3-yl)oxy)-2'-oxo-1',2'-dihydrospiro[cyclohexane-1,3'-indole]-5'-carboxylic acid | | 367.2 |

TABLE 5-8-continued

| Ex. No. | IUPAC name | structural formula | MS |
|---|---|---|---|
| 36 | (1r,4r)-4-((4,6-dimethylpyridin-3-yl)oxy)-2'-oxo-1',2'-dihydrospiro[cyclohexane-1,3'-indole]-5'-carboxylic acid | | 367.1 |
| 37 | (1r,4r)-4-(3,4-dihydro-2H-pyrano[2,3-b]pyridin-6-yloxy)-2'-oxo-1',2'-dihydrospiro[cyclohexane-1,3'-indole]-5'-carboxylic acid | | 395.2 |
| 38 | (1r,4r)-4-((4,6-dimethylpyrimidin-2-yl)oxy)-2'-oxo-1',2'-dihydrospiro[cyclohexane-1,3'-indole]-5'-carboxylic acid | | 368.2 |
| 39 | (1r,4r)-4-((5-chloro-4,6-dimethylpyrimidin-2-yl)oxy)-2'-oxo-1',2'-dihydrospiro[cyclohexane-1,3'-indole]-5'-carboxylic acid | | 400.1 |

TABLE 5-9

| Ex. No. | IUPAC name | structural formula | MS |
|---|---|---|---|
| 40 | (1r,4r)-4-((2,6-dimethylpyrimidin-4-yl)oxy)-2'-oxo-1',2'-dihydrospiro[cyclohexane-1,3'-indole]-5'-carboxylic acid | | 368.1 |
| 41 | (1r,4r)-4-(2-methylphenoxy)-2'-oxo-1',2'-dihydrospiro[cyclohexane-1,3'-indole]-5'-carboxylic acid | | 350.1 |
| 42 | (1r,4r)-4-(3-methylphenoxy)-2'-oxo-1',2'-dihydrospiro[cyclohexane-1,3'-indole]-5'-carboxylic acid | | 350.1 |
| 43 | (1r,4r)-4-(4-methylphenoxy)-2'-oxo-1',2'-dihydrospiro[cyclohexane-1,3'-indole]-5'-carboxylic acid | | 350 |

TABLE 5-9-continued

| Ex. No. | IUPAC name | structural formula | MS |
|---|---|---|---|
| 44 | (1r,4r)-4-(2-cyanophenoxy)-2'-oxo-1',2'-dihydrospiro[cyclohexane-1,3'-indole]-5'-carboxylic acid | | 363.2 |

TABLE 5-10

| Ex. No. | IUPAC name | structural formula | MS |
|---|---|---|---|
| 45 | (1r,4r)-4-(4-cyanophenoxy)-2'-oxo-1',2'-dihydrospiro[cyclohexane-1,3'-indole]-5'-carboxylic acid | | 361.1 |
| 46 | (1r,4r)-4-(3,4-dimethylphenoxy)-2'-oxo-1',2'-dihydrospiro[cyclohexane-1,3'-indole]-5'-carboxylic acid | | 364.1 |
| 47 | (1r,4r)-4-(2,4-dimethylphenoxy)-2'-oxo-1',2'-dihydrospiro[cyclohexane-1,3'-indole]-5'-carboxylic acid | | 364.1 |

TABLE 5-10-continued

| Ex. No. | IUPAC name | structural formula | MS |
|---|---|---|---|
| 48 | (1r,4r)-4-(3,5-dimethylphenoxy)-2'-oxo-1',2'-dihydrospiro[cyclohexane-1,3'-indole]-5'-carboxylic acid | | 364.1 |
| 49 | (1r,4r)-4-(4-methoxyphenxoy)-2'-oxo-1',2'-dihydrospiro[cyclohexane-1,3'-indole]-5'-carboxylic acid | | 366.1 |

TABLE 5-11

| Ex. No. | IUPAC name | structural formula | MS |
|---|---|---|---|
| 50 | (1r,4r)-4-(4-fluoro-2-methylphenoxy)-2'-oxo-1',2'-dihydrospiro[cyclohexane-1,3'-indole]-5'-carboxylic acid | | 368.1 |
| 51 | (1r,4r)-4-(4-fluoro-3-methylphenoxy)-2'-oxo-1',2'-dihydrospiro[cyclohexane-1,3'-indole]-5'-carboxylic acid | | 368.1 |

TABLE 5-11-continued

| Ex. No. | IUPAC name | structural formula | MS |
|---|---|---|---|
| 52 | (1r,4r)-4-(3-fluoro-4-methylphenoxy)-2'-oxo-1',2'-dihydrospiro[cyclohexane-1,3'-indole]-5'-carboxylic acid | | 368.1 |
| 53 | (1r,4r)-4-(2-fluoro-3-methylphenoxy)-2'-oxo-1',2'-dihydrospiro[cyclohexane-1,3'-indole]-5'-carboxylic acid | | 368.1 |
| 54 | (1r,4r)-4-(2-fluoro-4-methylphenoxy)-2'-oxo-1',2'-dihydrospiro[cyclohexane-1,3'-indole]-5'-carboxylic acid | | 368.2 |

TABLE 5-12

| Ex. No. | IUPAC name | structural formula | MS |
|---|---|---|---|
| 55 | (1r,4r)-4-(3,4-difluorophenoxy)-2'-oxo-1',2'-dihydrospiro[cyclohexane-1,3'-indole]-5'-carboxylic acid | | 372.3 |
| 56 | (1r,4r)-4-(2,5-difluorophenoxy)-2'-oxo-1',2'-dihydrospiro[cyclohexane-1,3'-indole]-5'-carboxylic acid | | 372.1 |
| 57 | (1r,4r)-4-(2,4-difluorophenoxy)-2'-oxo-1',2'-dihydrospiro[cyclohexane-1,3'-indole]-5'-carboxylic acid | | 372.1 |
| 58 | (1r,4r)-4-(3,5-difluorophenoxy)-2'-oxo-1',2'-dihydrospiro[cyclohexane-1,3'-indole]-5'-carboxylic acid | | 372.1 |

TABLE 5-12-continued

| Ex. No. | IUPAC name | structural formula | MS |
|---|---|---|---|
| 59 | (1r,4r)-4-(2,3-difluorophenoxy)-2'-oxo-1',2'-dihydrospiro[cyclohexane-1,3'-indole]-5'-carboxylic acid | | 372.1 |

TABLE 5-13

| Ex. No. | IUPAC name | structural formula | MS |
|---|---|---|---|
| 60 | (1r,4r)-4-(3-cyano-2-fluorophenoxy)-2'-oxo-1',2'-dihydrospiro[cyclohexane-1,3'-indole]-5'-carboxylic acid | | 379.2 |
| 61 | (1r,4r)-4-(4-cyano-3-fluorophenoxy)-2'-oxo-1',2'-dihydrospiro[cyclohexane-1,3'-indole]-5'-carboxylic acid | | 379.1 |
| 62 | (1r,4r)-4-(2-cyano-6-fluorophenoxy)-2'-oxo-1',2'-dihydrospiro[cyclohexane-1,3'-indole]-5'-carboxylic acid | | 381.1 |
| 63 | (1r,4r)-4-(2-cyano-3-fluorophenoxy)-2'-oxo-1',2'-dihydrospiro[cyclohexane-1,3'-indole]-5'-carboxylic acid | | 381.1 |
| 64 | (1r,4r)-4-(3-chloro-5-fluorophenoxy)-2'-oxo-1',2'-dihydrospiro[cyclohexane-1,3'-indole]-5'-carboxylic acid | | 388.1 |

TABLE 5-14

| Ex. No. | IUPAC name | structural formula | MS |
|---|---|---|---|
| 65 | (1r,4r)-4-(2-chloro-5-fluorophenoxy)-2'-oxo-1',2'-dihydrospiro[cyclohexane-1,3'-indole]-5'-carboxylic acid | | 388.1 |

TABLE 5-14-continued

| Ex. No. | IUPAC name | structural formula | MS |
|---|---|---|---|
| 66 | (1r,4r)-4-(4-chloro-2-fluorophenoxy)-2'-oxo-1',2'-dihydrospiro[cyclohexane-1,3'-indole]-5'-carboxylic acid | | 388 |
| 67 | (1r,4r)-4-(3-chloro-4-fluorophenoxy)-2'-oxo-1',2'-dihydrospiro[cyclohexane-1,3'-indole]-5'-carboxylic acid | | 388.1 |
| 68 | (1r,4r)-4-(2-chloro-4-fluorophenoxy)-2'-oxo-1',2'-dihydrospiro[cyclohexane-1,3'-indole]-5'-carboxylic acid | | 388.1 |
| 69 | (1r,4r)-4-(4-chloro-3-fluorophenoxy)-2'-oxo-1',2'-dihydrospiro[cyclohexane-1,3'-indole]-5'-carboxylic acid | | 388 |

TABLE 5-15

| Ex. No. | IUPAC name | structural formula | MS |
|---|---|---|---|
| 70 | (1r,4r)-4-(2-cyano-4-methoxyphenoxy)-2'-oxo-1',2'-dihydrospiro[cyclohexane-1,3'-indole]-5'-carboxylic acid | | 393.2 |

TABLE 5-15-continued

| Ex. No. | IUPAC name | structural formula | MS |
|---|---|---|---|
| 71 | (1r,4r)-4-(4-chloro-3-cyanophenoxy)-2'-oxo-1',2'-dihydrospiro[cyclohexane-1,3'-indole]-5'-carboxylic acid | | 395.1 |
| 72 | (1r,4r)-4-(2-chloro-4-cyanophenoxy)-2'-oxo-1',2'-dihydrospiro[cyclohexane-1,3'-indole]-5'-carboxylic acid | | 395.1 |
| 73 | (1r,4r)-4-(3-chloro-4-cyanophenoxy)-2'-oxo-1',2'-dihydrospiro[cyclohexane-1,3'-indole]-5'-carboxylic acid | | 395.1 |
| 74 | (1r,4r)-2'-oxo-4-(2-(trifluoromethyl)phenoxy)-1',2'-dihydrospiro[cyclohexane-1,3'-indole]-5'-carboxylic acid | | 404.1 |

TABLE 5-16

| Ex. No. | IUPAC name | structural formula | MS |
|---|---|---|---|
| 75 | (1r,4r)-2'-oxo-4-(3-(trifluoromethyl)phenoxy)-1',2'-dihydrospiro[cyclohexane-1,3'-indole]-5'-carboxylic acid | | 404.2 |
| 76 | (1r,4r)-4-(3-fluoro-5-(trifluoromethyl)phenoxy)-2'-oxo-1',2'-dihydrospiro[cyclohexane-1,3'-indole]-5'-carboxylic acid | | 422.1 |
| 77 | (1r,4r)-4-(2-fluoro-3-(trifluoromethyl)phenoxy)-2'-oxo-1',2'-dihydrospiro[cyclohexane-1,3'-indole]-5'-carboxylic acid | | 422.1 |

TABLE 5-16-continued

| Ex. No. | IUPAC name | structural formula | MS |
|---|---|---|---|
| 78 | (1r,4r)-4-(2-fluoro-5-(trifluoromethyl)phenoxy)-2'-oxo-1',2'-dihydrospiro[cyclohexane-1,3'-indole]-5'-carboxylic acid | | 422.1 |
| 79 | (1r,4r)-4-(4-fluoro-3-(trifluoromethyl)phenoxy)-2'-oxo-1',2'-dihydrospiro[cyclohexane-1,3'-indole]-5'-carboxylic acid | | 422.1 |

TABLE 5-17

| Ex. No. | IUPAC name | structural formula | MS |
|---|---|---|---|
| 80 | (1r,4r)-4-((1-methyl-5-(trifluoromethyl)-1H-pyrazol-3-yl)oxy)-2'-oxo-1',2'-dihydrospiro[cyclohexane-1,3'-indole]-5'-carboxylic acid | | 410.1 |

TABLE 5-17-continued

| Ex. No. | IUPAC name | structural formula | MS |
|---|---|---|---|
| 81 | (1s,4s)-4-((5-chloro-3-methylpyridin-2-yl)oxy)-2'-oxo-1',2'-dihydrospiro[cyclohexane-1,3'-pyrrolo[3,2-b]pyridine]-5'-carboxylic acid | 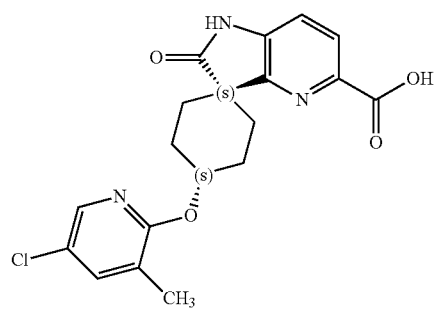 | 385.6 |
| 82 | (1r,4r)-4-(4-chloro-2-methoxyphenoxy)-2'-oxo-1',2'-dihydrospiro[cyclohexane-1,3'-indole]-5'-carboxylic acid | 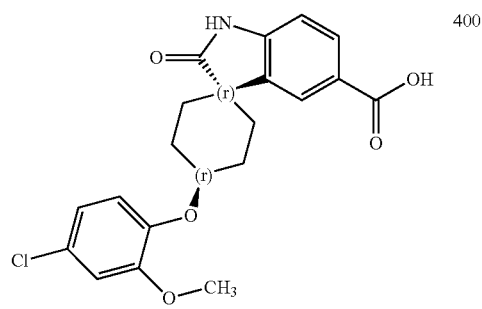 | 400 |
| 83 | (1s,4s)-4-(4-chloro-2-methoxyphenoxy)-2'-oxo-1',2'-dihydrospiro[cyclohexane-1,3'-indole]-5'-carboxylic acid | 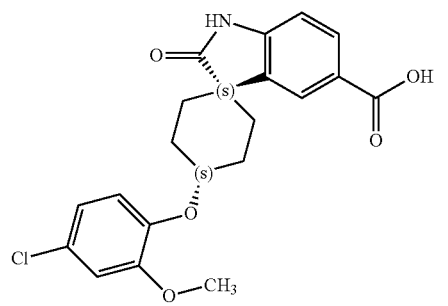 | 402.1 |
| 84 | (1s,4s)-4-(2,4-difluorophenoxy)-2'-oxo-1',2'-dihydrospiro[cyclohexane-1,3'-pyrrolo[3,2-b]pyridine]-5'-carboxylic acid | 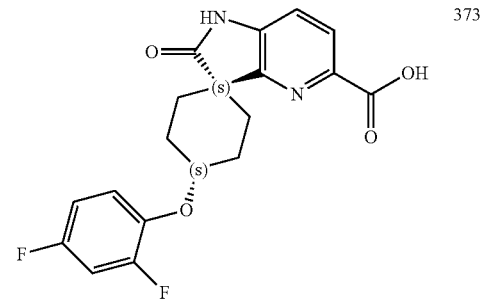 | 373 |

TABLE 5-18

| Ex. No. | IUPAC name | structural formula | MS |
|---|---|---|---|
| 85 | (1s,4s)-4-(2-chlorophenoxy)-2'-oxo-1',2'-dihydrospiro[cyclohexane-1,3'-pyrrolo[3,2-b]pyridine]-5'-carboxylic acid | | 370.9 |
| 86 | (1s,4s)-4-(4-chloro-2,6-difluorophenoxy)-2'-oxo-1',2'-dihydrospiro[cyclohexane-1,3'-pyrrolo[3,2-b]pyridine]-5'-carboxylic acid | | 406.9 |
| 87 | (1s,4s)-4-((5-chloro-3-fluoropyridin-2-yl)oxy)-2'-oxo-1',2'-dihydrospiro[cyclohexane-1,3'-indole]-5'-carboxylic acid | | 391.1 |
| 88 | (1s,4s)-4-(4-chlorophenoxy)-2'-oxo-1',2'-dihydrospiro[cyclohexane-1,3'-pyrrolo[3,2-b]pyridine]-5'-carboxylic acid | | 370.9 |
| 89 | (1s,4s)-4-(4-chloro-2,6-dimethylphenoxy)-2'-oxo-1',2'-dihydrospiro[cyclohexane-1,3'-pyrrolo[3,2-b]pyridine]-5'-carboxylic acid | | 399 |

TABLE 5-19

| Ex. No. | IUPAC name | structural formula | MS |
|---|---|---|---|
| 90 | (1r,4r)-4-(2-chlorophenoxy)-2'-oxo-1',2'-dihydrospiro[cyclohexane-1,3'-pyrrolo[3,2-b]pyridine]-5'-carboxylic acid | | 373.1 |
| 91 | (1r,4r)-4-(2,4-difluorophenoxy)-2'-oxo-1',2'-dihydrospiro[cyclohexane-1,3'-pyrrolo[3,2-b]pyridine]-5'-carboxylic acid | | 375.1 |
| 92 | (1r,4r)-4-(4-chlorophenoxy)-2'-oxo-1',2'-dihydrospiro[cyclohexane-1,3'-pyrrolo[3,2-b]pyridine]-5'-carboxylic acid | | 373.1 |
| 93 | (1r,4r)-4-(4-chloro-2,6-difluorophenoxy)-2'-oxo-1',2'-dihydrospiro[cyclohexane-1,3'-pyrrolo[3,2-b]pyridine]-5'-carboxylic acid | | 407 |
| 94 | (1r,4r)-4-(4-chloro-2,6-dimethylphenoxy)-2'-oxo-1',2'-dihydrospiro[cyclohexane-1,3'-pyrrolo[3,2-b]pyridine]-5'-carboxylic acid | | 401.1 |

TABLE 5-20

| Ex. No. | IUPAC name | structural formula | MS |
|---|---|---|---|
| 95 | (1r,4r)-4-(4-chloro-2-(trifluoromethyl)phenoxy)-2'-oxo-1',2'-dihydrospiro[cyclohexane-1,3'-pyrrolo[3,2-b]pyridine]-5'-carboxylic acid | | 439 |
| 96 | (1s,4s)-4-(4-chloro-2-(trifluoromethyl)phenoxy)-2'-oxo-1',2'-dihydrospiro[cyclohexane-1,3'-pyrrolo[3,2-b]pyridine]-5'-carboxylic acid | | 439 |
| 97 | (1s,4s)-4-((3,5-dichloropyridin-2-yl)oxy)-2'-oxo-1',2'-dihydrospiro[cyclohexane-1,3'-pyrrolo[3,2-b]pyridine]-5'-carboxylic acid | | 405.9 |
| 98 | (1r,4r)-4-((3,5-dichloropyridin-2-yl)oxy)-2'-oxo-1',2'-dihydrospiro[cyclohexane-1,3'-pyrrolo[3,2-b]pyridine]-5'-carboxylic acid | | 408 |

TABLE 5-20-continued

| Ex. No. | IUPAC name | structural formula | MS |
|---|---|---|---|
| 99 | (1r,4r)-4-((5-chloro-3-(trifluoromethyl)pyridin-2-yl)oxy)-2'-oxo-1',2'-dihydrospiro[cyclohexane-1,3'-pyrrolo[3,2-b]pyridine]-5'-carboxylic acid | | 440 |

TABLE 5-21

| Ex. No. | IUPAC name | structural formula | MS |
|---|---|---|---|
| 100 | (1s,4s)-4-((5-chloro-3-fluoropyridin-2-yl)oxy)-2'-oxo-1',2'-dihydrospiro[cyclohexane-1,3'-pyrrolo[3,2-b]pyridine]-5'-carboxylic acid | | 389.9 |
| 101 | (1s,4s)-4-(2,4-dichlorophenoxy)-2'-oxo-1',2'-dihydrospiro[cyclohexane-1,3'-pyrrolo[3,2-b]pyridine]-5'-carboxylic acid | | 404.9 |
| 102 | (1r,4r)-4-(2,4-dichlorophenoxy)-2'-oxo-1',2'-dihydrospiro[cyclohexane-1,3'-pyrrolo[3,2-b]pyridine]-5'-carboxylic acid | | 407 |

TABLE 5-21-continued

| Ex. No. | IUPAC name | structural formula | MS |
|---|---|---|---|
| 103 | (1s,4s)-4-((3-methyl-5-(trifluoromethyl)pyridin-2-yl)oxy)-2'-oxo-1',2'-dihydrospiro[cyclohexane-1,3'-pyrrolo[3,2-b]pyridine]-5'-carboxylic acid | | 420.1 |
| 104 | (1s,4s)-4-((3-cyano-6-methylpyridin-2-yl)oxy)-2'-oxo-1',2'-dihydrospiro[cyclohexane-1,3'-indole]-5'-carboxylic acid | | 376 |

TABLE 5-22

| Ex. No. | IUPAC name | structural formula | MS |
|---|---|---|---|
| 105 | (1r,4r)-4-((3-chloro-5-(trifluoromethyl)pyridin-2-yl)oxy)-2'-oxo-1',2'-dihydrospiro[cyclohexane-1,3'-pyrrolo[3,2-b]pyridine]-5'-carboxylic acid | | 440 |
| 106 | (1s,4s)-4-((5-chloro-3-cyano-4-methylpyridin-2-yl)oxy)-2'-oxo-1',2'-dihydrospiro[cyclohexane-1,3'-pyrrolo[3,2-b]pyridine]-5'-carboxylic acid | | 411.1 |

TABLE 5-22-continued

| Ex. No. | IUPAC name | structural formula | MS |
|---|---|---|---|
| 107 | (1s,4s)-2'-oxo-4-phenoxy-1',2'-dihydrospiro[cyclohexane-1,3'-indole]-5'-carboxylic acid | | 336 |
| 108 | (1s,4s)-4-(4-chlorophenoxy)-2'-oxo-1',2'-dihydrospiro[cyclohexane-1,3'-indole]-5'-carboxylic acid | | 370.1 |
| 109 | (1r,4r)-4-((5-cyclopropyl-3-(trifluoromethyl)pyridin-2-yl)oxy)-2'-oxo-1',2'-dihydrospiro[cyclohexane-1,3'-pyrrolo[3,2-b]pyridine]-5'-carboxylic acid | | 446.1 |

TABLE 5-23

| Ex. No. | IUPAC name | structural formula | MS |
|---|---|---|---|
| 110 | (1s,4s)-4-((5-chloro-3-cyanopyridin-2-yl)oxy)-2'-oxo-1',2'-dihydrospiro[cyclohexane-1,3'-pyrrolo[3,2-b]pyridine]-5'-carboxylic acid | | 397.1 |

TABLE 5-23-continued

| Ex. No. | IUPAC name | structural formula | MS |
|---|---|---|---|
| 111 | (1s,4s)-4-((3-chloro-5-cyclopropylpyridin-2-yl)oxy)-2'-oxo-1',2'-dihydrospiro[cyclohexane-1,3'-pyrrolo[3,2-b]pyridine]-5'-carboxylic acid | 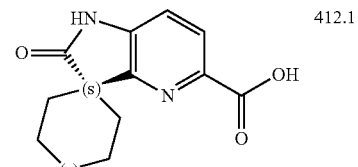 | 412.1 |
| 112 | (1r,4r)-4-((3-methyl-5-(trifluoromethyl)pyridin-2-yl)oxy)-2'-oxo-1',2'-dihydrospiro[cyclohexane-1,3'-pyrrolo[3,2-b]pyridine]-5'-carboxylic acid | 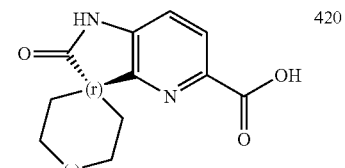 | 420 |
| 113 | (1r,4r)-2'-oxo-4-phenoxy-1',2'-dihydrospiro[cyclohexane-1,3'-indole]-5'-carboxylic acid | 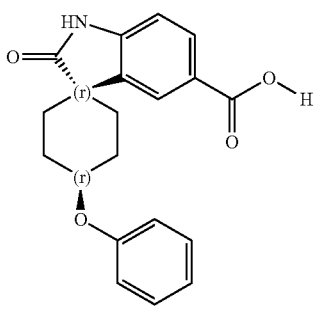 | 335.9 |
| 114 | (1r,4r)-4-(4-chlorophenoxy)-2'-oxo-1',2'-dihydrospiro[cyclohexane-1,3'-indole]-5'-carboxylic acid | 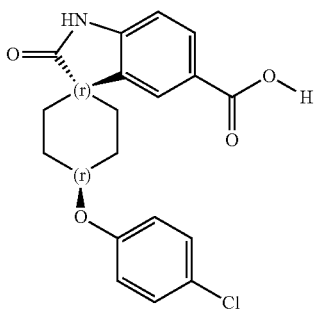 | 370 |

TABLE 5-24

| Ex. No. | IUPAC name | structural formula | MS |
|---|---|---|---|
| 115 | (1s,4s)-4-((3-chloro-5-(trifluoromethyl)pyridin-2-yl)oxy)-2'-oxo-1',2'-dihydrospiro[cyclohexane-1,3'-pyrrolo[3,2-b]pyridine]-5'-carboxylic acid | | 440 |

Experimental Example 1

IP6K Enzyme Inhibitory Assay

Method

Human IP6K1 and human IP6K2 enzymes were prepared by transducing human IP6K1 (1-441) gene or human IP6K2 (1-426) gene into Sf-9 insect cells and purifying by GST affinity column. Human IP6K3 enzyme was prepared by transducing human IP6K3 (1-410) gene into BL21 (DE3) *Escherichia coli* and purifying by Ni-NTA (nickel-nitrilotriacetic acid) affinity column. Rat IP6K3 and mouse IP6K3 enzymes were prepared by transducing rat IP6K3 (1-401) gene or mouse IP6K3 (1-396) gene into FreeStyle™293 cells and purifying by GST affinity column. The enzymes were used after preservation at −70° C. The IP6K enzyme inhibitory activity of the test compound was measured by the following experiment method and using ADP-Glo™ Kinase Assay (manufactured by Promega). A test compound diluted with an assay buffer (20 mM HEPES (pH 7.5), 6 mM $MgCl_2$, 0.01% Tween-20, 1 mM DTT) was first added by 2 μL to a 384 well plate. Then, ATP.IP6 substrate mixed solution (human IP6K1, IP6K2, IP6K3: ATP.IP6=135 μM.45 μM, rat IP6K3: ATP.IP6=300 μM.4.5 μM, mouse IP6K3: ATP.IP6=150 μM.15 μM) was added by 2 μL. The IP6K enzyme solution diluted with the assay buffer was added by 2 μL to start the enzyme reaction. Incubation was performed at room temperature for a given time (120 min for rat IP6K3 alone, 60 min for others). After incubation at room temperature, ADP-Glo solution prepared according to the protocol of Promega was added by 3 μL to the 384 well plate and reacted at room temperature for 30 min. Thereafter, Kinase-Detection solution was added by 6 μL to the 384 well plate and reacted at room temperature for 60 min. After the reaction, the luminescence intensity was measured by a plate reader Envision (manufactured by PerkinElmer). The inhibitory activity of each compound was calculated as a relative activity value to luminescence intensity of the well without enzyme as 100% inhibition. The results are shown in Table 6.

TABLE 6

IP6K inhibitory activity of Example compounds
ADP-Glo method inhibitory rate (%)
at compound concentration 0.1 μM

| Example | human IP6K1 | human IP6K2 | human IP6K3 |
|---|---|---|---|
| 1 | 100 | 100 | 99 |
| 2 | 101 | 94 | 100 |
| 3 | 101 | 101 | 85 |
| 4 | 66 | 79 | 99 |
| 5 | 86 | 89 | 94 |
| 6 | 96 | 93 | 97 |
| 7 | 100 | 101 | 86 |
| 8 | 100 | 97 | 95 |
| 9 | 98 | 101 | 94 |
| 10 | 98 | 100 | 102 |
| 11 | 100 | 97 | 102 |
| 12 | 95 | 97 | 101 |
| 13 | 100 | 97 | 100 |
| 14 | 100 | 100 | 90 |
| 15 | 99 | 101 | 91 |
| 16 | 99 | 89 | 98 |
| 17 | 92 | 91 | 93 |
| 18 | 54 | 62 | 77 |
| 19 | 40 | 45 | 70 |
| 20 | 79 | 95 | 98 |
| 21 | 79 | 91 | 96 |
| 22 | 72 | 72 | 90 |
| 23 | 72 | 79 | 92 |
| 24 | 86 | 92 | 92 |
| 25 | 95 | 97 | 98 |
| 26 | 98 | 97 | 92 |
| 27 | 97 | 93 | 96 |
| 28 | 95 | 98 | 96 |
| 29 | 99 | 96 | 99 |
| 30 | 81 | 84 | 97 |
| 31 | 101 | 101 | 100 |
| 32 | 63 | 67 | 88 |
| 33 | 37 | 40 | 74 |
| 34 | 63 | 76 | 91 |
| 35 | 82 | 96 | 98 |
| 36 | 72 | 92 | 95 |
| 37 | 51 | 50 | 82 |
| 38 | 55 | 47 | 86 |
| 39 | 80 | 74 | 95 |
| 40 | 14 | 18 | 49 |
| 41 | 93 | 93 | 98 |
| 42 | 81 | 90 | 97 |
| 43 | 98 | 99 | 100 |
| 44 | 88 | 83 | 94 |
| 45 | 96 | 93 | 97 |
| 46 | 97 | 98 | 99 |
| 47 | 99 | 96 | 99 |
| 48 | 86 | 91 | 97 |
| 49 | 100 | 99 | 100 |
| 50 | 101 | 100 | 96 |
| 51 | 98 | 97 | 96 |
| 52 | 99 | 100 | 96 |
| 53 | 96 | 96 | 97 |
| 54 | 99 | 100 | 101 |
| 55 | 96 | 95 | 99 |

TABLE 6-continued

IP6K inhibitory activity of Example compounds
ADP-Glo method inhibitory rate (%)
at compound concentration 0.1 μM

| Example | human IP6K1 | human IP6K2 | human IP6K3 |
|---|---|---|---|
| 56 | 97 | 92 | 99 |
| 57 | 99 | 97 | 100 |
| 58 | 72 | 83 | 90 |
| 59 | 87 | 86 | 97 |
| 60 | 87 | 90 | 98 |
| 61 | 100 | 95 | 100 |
| 62 | 95 | 91 | 99 |
| 63 | 69 | 87 | 96 |
| 64 | 80 | 93 | 94 |
| 65 | 93 | 95 | 97 |
| 66 | 99 | 100 | 96 |
| 67 | 93 | 98 | 97 |
| 68 | 93 | 98 | 98 |
| 69 | 100 | 100 | 96 |
| 70 | 99 | 99 | 99 |
| 71 | 88 | 90 | 95 |
| 72 | 99 | 97 | 97 |
| 73 | 98 | 97 | 91 |
| 74 | 93 | 92 | 92 |
| 75 | 89 | 94 | 89 |
| 76 | 81 | 86 | 86 |
| 77 | 94 | 99 | 98 |
| 78 | 96 | 96 | 98 |
| 79 | 87 | 89 | 97 |
| 80 | 62 | 82 | 89 |
| 81 | 96 | 100 | 100 |
| 82 | 98 | 101 | 99 |
| 83 | 97 | 100 | 102 |
| 84 | 75 | 59 | 91 |
| 85 | 81 | 71 | 95 |
| 86 | 55 | 50 | 80 |
| 87 | 107 | 102 | 102 |
| 88 | 101 | 97 | 97 |
| 89 | 9 | 14 | 26 |
| 90 | 49 | 47 | 61 |
| 91 | 69 | 60 | 79 |
| 92 | 97 | 92 | 98 |
| 93 | 92 | 96 | 101 |
| 94 | 91 | 97 | 101 |
| 95 | 88 | 91 | 96 |
| 96 | 95 | 99 | 101 |
| 97 | 101 | 101 | 110 |
| 98 | 91 | 94 | 107 |
| 99 | 51 | 64 | 83 |
| 100 | 76 | 98 | 97 |
| 101 | 104 | 100 | 98 |
| 102 | 105 | 94 | 97 |
| 103 | 98 | 99 | 99 |
| 104 | 95 | 99 | 98 |
| 105 | 86 | 94 | 95 |
| 106 | 96 | 97 | 95 |
| 107 | 94 | 93 | 92 |
| 108 | 97 | 101 | 99 |
| 109 | 94 | 95 | 95 |
| 110 | 84 | 96 | 96 |
| 111 | 91 | 99 | 98 |
| 112 | 90 | 90 | 97 |
| 113 | 79 | 79 | 85 |
| 114 | 99 | 101 | 96 |
| 115 | 97 | 99 | 99 |

Experimental Example 2

Tissue IP7 Lowering Effect in Rat
Method
Vehicle (0.5% methyl cellulose) and compound 97 (compound of Example 97) were orally administered at 1, 3, 10 mg/kg to 20-week-old male Zucker fatty rats (obtained from TAKEDA RABICS), and the IP7 level of the liver, skeletal muscle (soleus muscle) and fat (epididymal fat) was measured 6 and 24 hr later.

IP7 Measurement Method
Extraction 1
To cryopreserved tissues was added 1.0 mL of an aqueous solution of 1N sodium hydroxide/0.2 M ethylenediaminetetraacetic acid per 100 mg of the tissue, pulverized with zirconia beads under 4° C. condition and stood on ice for 1 hr. 0.1 mL of 25% acetic acid was added per 0.4 mL of the pulverized liquid, and they were mixed and centrifuged (15000 rpm, 5 min, 4° C.). Then, the supernatant was subjected to ultrafiltration (13000 rpm, 5 min, 4° C.; microcon YM-3 membrane centrifugal filter unit (Millipore)). The passage fraction was recovered, equal amounts of 1.5% acetic acid/1.5% aqueous octylamine solution were added and the mixture was stirred by Vortex and 0.05 mL was injected into LC/MS/MS.
Extraction 2
To cryopreserved tissues was added 0.3 mL of 3.6% perchloric acid per 100 mg of the tissue and the mixture was pulverized with zirconia beads under 4° C. condition. Then, 0.1 mL of 30% aqueous potassium chloride solution was added per 0.3 mL of 3.6% perchloric acid added, and they were mixed and centrifuged (15000 rpm, 5 min, 4° C.). Then, the supernatant was subjected to ultrafiltration (13000 rpm, 5 min, 4° C.; microcon YM-3 membrane centrifugal filter unit (Millipore)). The passage fraction was recovered, equal amounts of 1.5% acetic acid/1.5% aqueous octylamine solution were added and the mixture was stirred by Vortex and 0.01 mL was injected into LC/MS/MS.

Samples subjected to a protein removal treatment by the methods of extraction 1 and extraction 2 were measured by the LC/MS/MS system containing Nexera UHPLC system (Shimadzu Corporation) and QTRAP (registered trademark) 5500 mass spectrometer system (SCIEX) in combination. The column used was Triat PEEK column (30×2.1 mm, 3 μm, GL Sciences Inc.), solvent A used was an aqueous solution of 0.1% ammonia/0.01% octylamine/10 μM ethylenediaminetetraacetic acid and solvent B used was 0.01% ammonia/0.002% octylamine/methanol solution. The flow rate was set to 0.7 mL per min, the column temperature was set to 50° C., the ratio of solvent B to solvent A was set to the following and inositolpolyphosphoric acid was separated on chromatography. After injecting the sample, the measurement was performed at 2% isocratic for 0-0.5 min, 2% to 50% gradient for 0.5-2 min, 50% to 90% gradient for 2-5 min, 90% isocratic for 5-6 min and 2% isocratic for 6-8 min. The eluate was ionized in the negative ion mode by mass spectrometry and ion intensity of the measurement target molecule was measured under the MRM conditions in Table 7. The conditions of the instrument were ion spray voltage 4500 V, turbo probe temperature 400° C., heat gas 40 L per min, nitrogen 12 L per min as curtain gas, multiplier 2100 V, declustering potential −80 V, collision cell exit potential −11V.

TABLE 7

| measurement target molecule | Precursor ion (m/z) | Product ion (m/z) | CE (V) | elution time (min) |
|---|---|---|---|---|
| IP5 | 579 | 481 | −38 | 3.89 |
| IP6 | 659 | 561 | −35 | 4.01 |
| IP7 | 739 | 641 | −35 | 4.08 |
|  | 739 | 159 | −85 | 4.08 |
| IP8 | 819 | 721 | −38 | 4.11 |

CE; collision energy

The area value of the mass chromatogram obtained by the measurement was calculated by MultiQuant ver 3.0 (SCIEX).

Results

Figure 2:
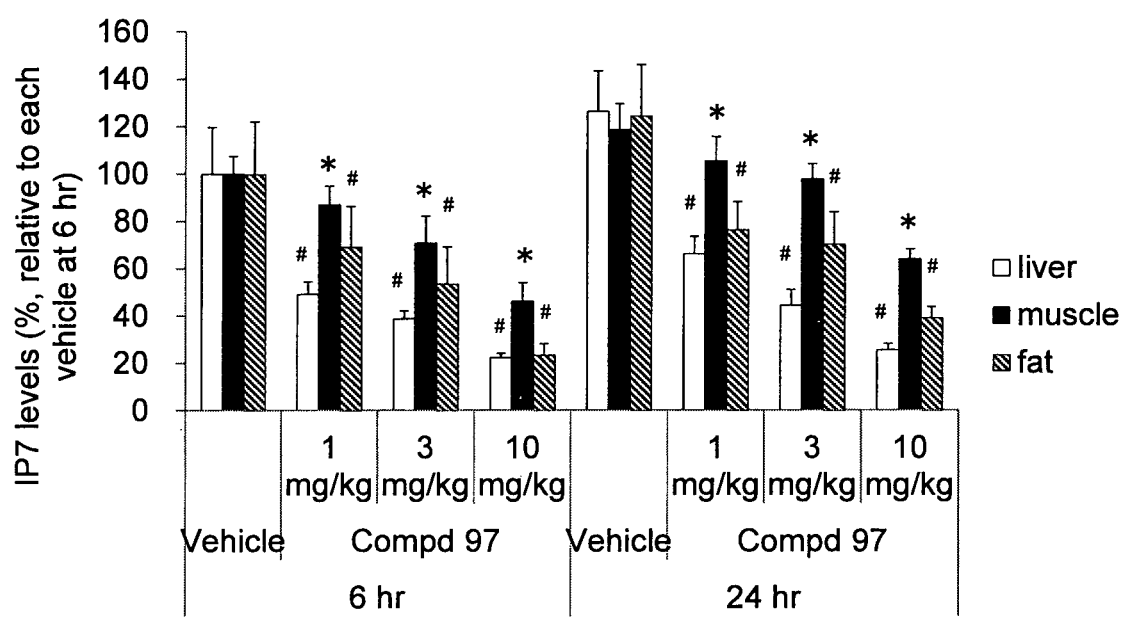
FIG. 2 shows IP7 levels of the liver, muscle and fat of a rat by administration of compound 97.

The results are shown in FIG. 2. Compound 97 showed a dose-dependent and sustained decrease in the IP7 level of the liver, muscle and fat.

*p<0.025 vs vehicle-treated rat by one-tailed Williams' test
p<0.025 vs vehicle-treated rat by one-tailed Shirley Williams test Experimental Example 3

Non-Fasting Hyperglycemic Lowering Effect in Diabetes Rat

Method

Vehicle (0.5% methyl cellulose), compound 97 at 3 or 10 mg/kg and metformin at 150 mg/kg were orally administered to 12-week-old male Zucker fatty rats having equalized glycosylated hemoglobin, body weight and non-fasting blood glucose (n=6, Zucker lean rats (n=4) obtained from CHARLES RIVER LABORATORIES JAPAN, INC. as normal control) and the blood glucose level was measured for 24 hr.

Results

Figure 3:
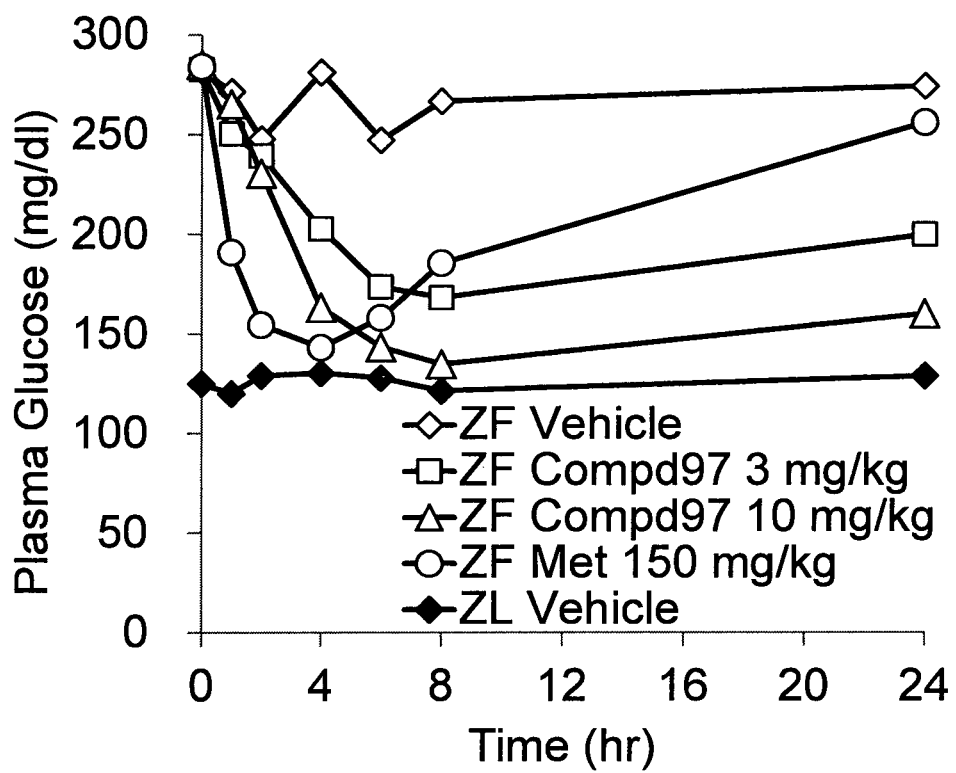
FIG. 3 shows plasma glucose of a diabetes model rat for up to 24 hr after oral administration.
Figure 4:
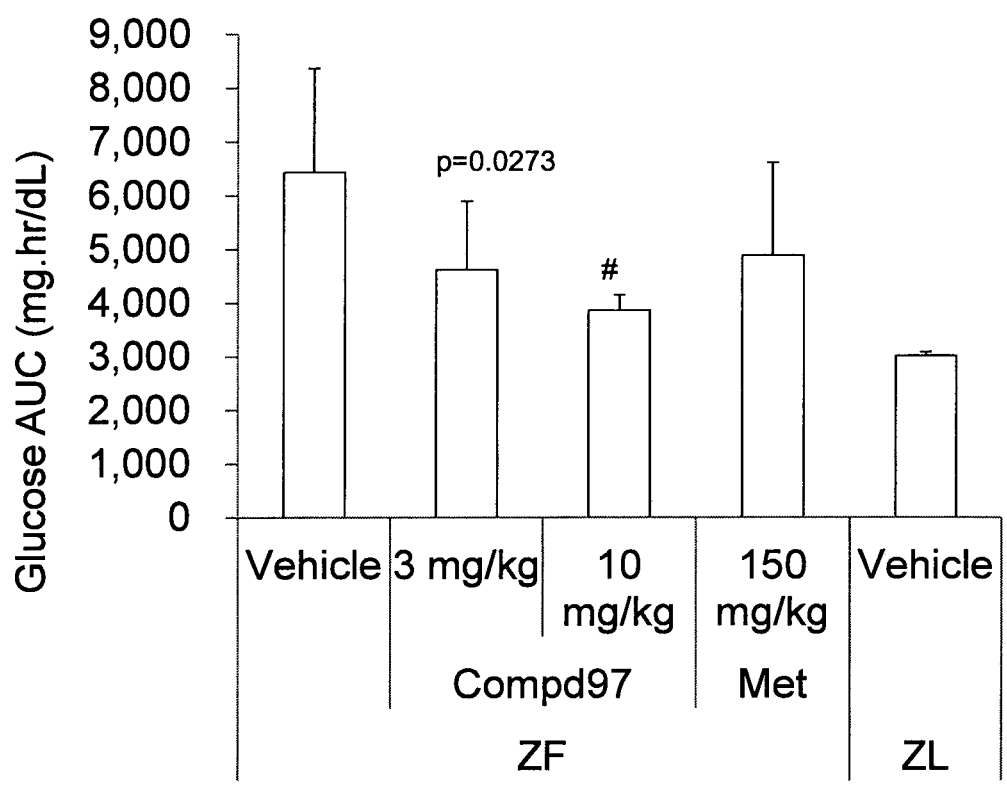
FIG. 4 shows glucose AUC (area under curve) of a diabetes model rat for up to 24 hr after oral administration.
Figure 5:
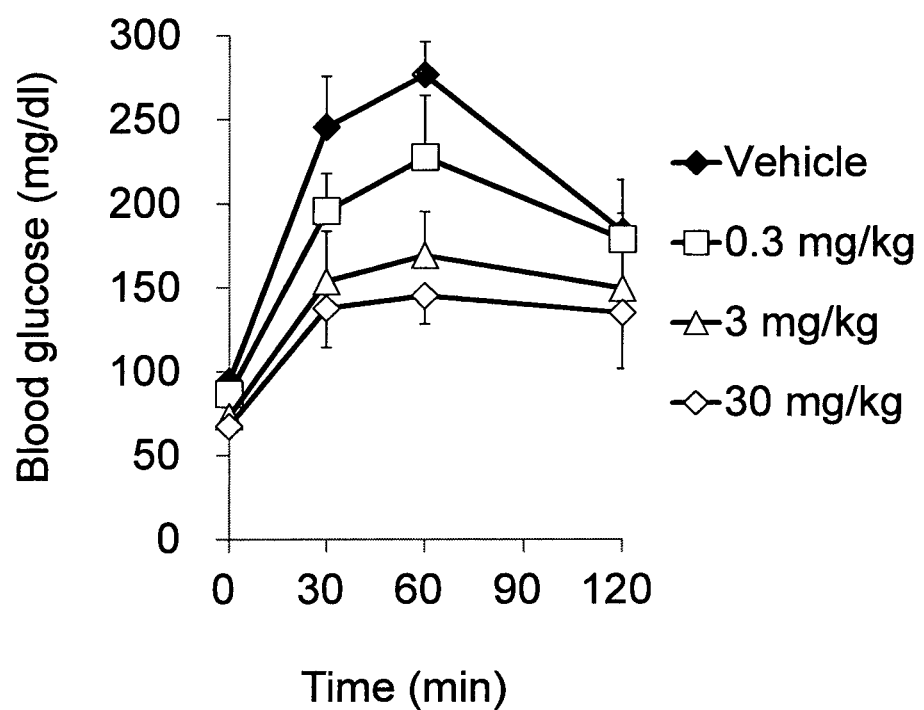
FIG. 5 shows blood glucose of a rat with impaired glucose tolerance for up to 120 min after administration of compound 9.
Figure 6:
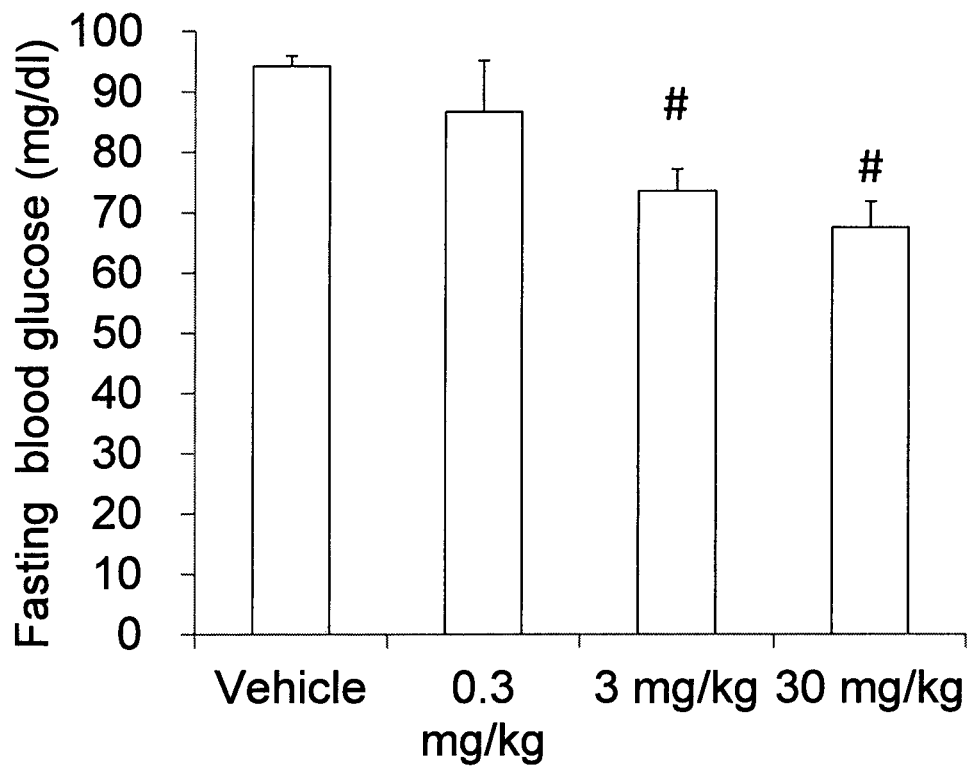
FIG. 6 shows blood glucose during fasting of a rat with impaired glucose tolerance after administration of compound 9.
Figure 7:
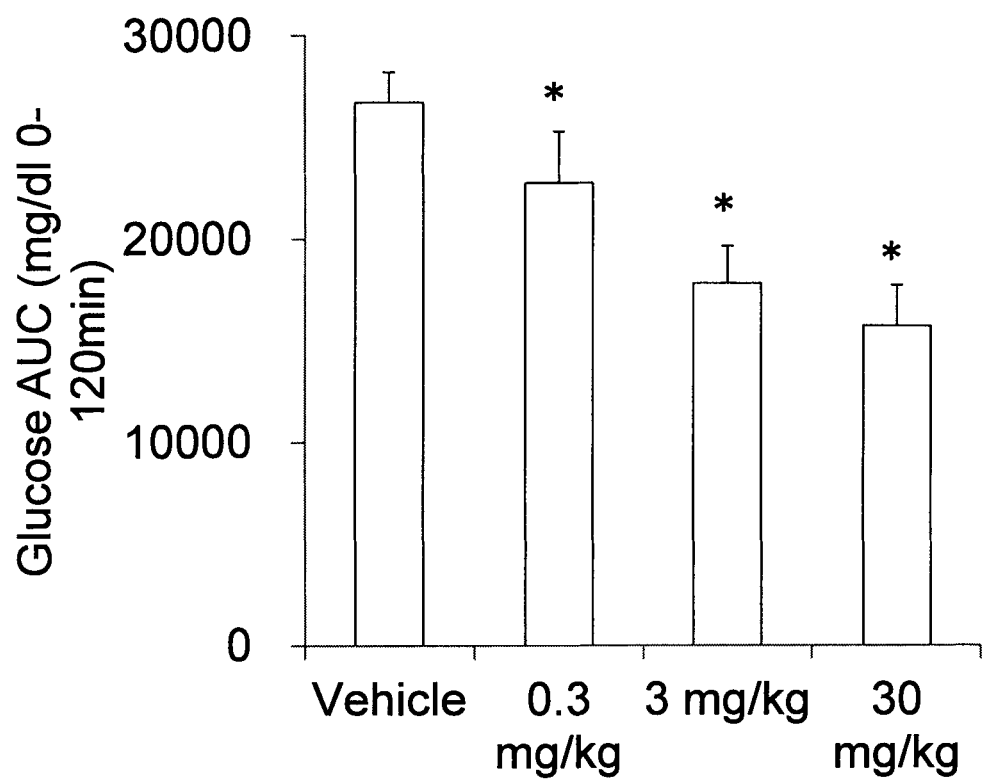
FIG. 7 shows glucose AUC of a rat with impaired glucose tolerance for up to 120 min after administration of compound 9.
Figure 8:
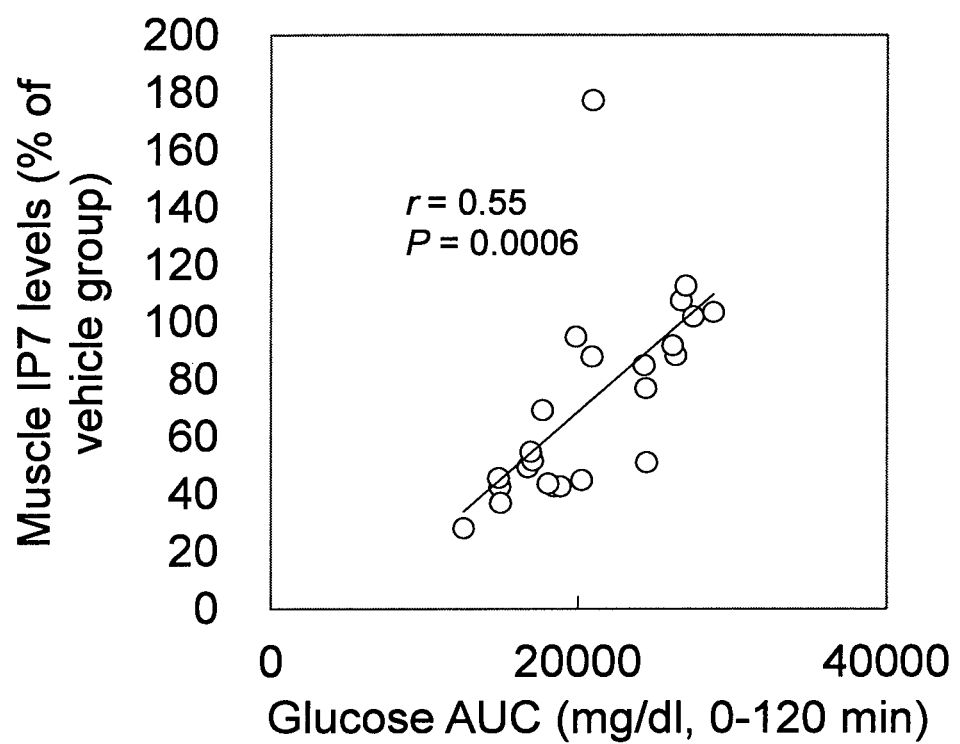
FIG. 8 shows correlation between glucose AUC and IP7 level of muscle of a rat with impaired glucose tolerance after administration of compound 9.
Figure 9:
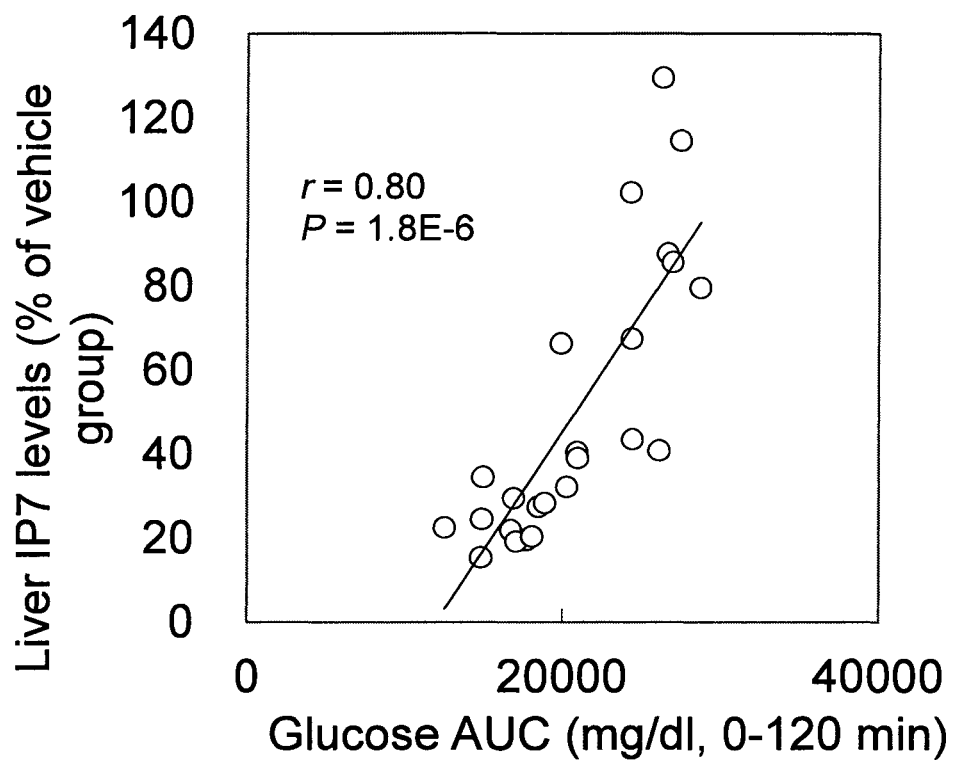
FIG. 9 shows correlation between glucose AUC and 127 level of the liver of a rat with impaired glucose tolerance after administration of compound 9.

The results are shown in FIG. 3 and FIG. 4. Compound 97 showed a sustained lowering effect on hyperglycemia during non-fasting and a significant hypoglycemic action (decrease in glucose AUC up to 24 hr) was confirmed in compound 97 (10 mg/kg) administration group.

Mean±SD, n=6(ZF) and 4(ZL)
ZF: Zucker fatty
ZL: Zucker lean
Compd 97: compound 97
Met: Metformin
p<0.025 vs vehicle-treated ZF rat by Shirley Williams test Experimental Example 4

Glucose Tolerance Improving Effect and Decrease in Tissue IP7 in Rat with Impaired Glucose Tolerance Method Vehicle (0.5% methyl cellulose) or compound 9 (compound of Example 9) at 0.3, 3, and 30 mg/kg was orally administered to 17-week-old male Zucker fatty rats (n=6, obtained from Takeda RABICS)) having equalized glycosylated hemoglobin and body weight and the rats were fasted for 16 hr. Then, fasting blood glucose was measured, glucose was orally loaded (2 g/kg) and the blood glucose level was measured for 120 min. After blood sample collection for 120 min, tissues (soleus muscle and liver) were promptly collected and the content of 127 in the tissue was measured.

Results

The results are shown in FIG. 5-FIG. 9. In rats with impaired glucose tolerance, administration of compound 9 decreased fasting blood glucose from 3 mg/kg and improved glucose tolerance from 0.3 mg/kg (glucose AUC in 0-120 min). The glucose tolerance-improving effect (glucose AUC in 0-120 min) correlated well with the decrease in 127 in the muscle (soleus muscle) and liver.

Mean±SD, n=6.
*p<0.025 vs vehicle-treated ZF rat by one-tailed Williams' test
p<0.025 vs vehicle-treated ZF rat by one-tailed Shirley Williams Test Experimental Example 5

Life Prolonging Effect in Cardiac Failure Model Mouse

Method

Vehicle (0.5% methylcellulose solution), compound 97 (10 mg/kg) and compound 9 (10 mg/kg) were orally administered once per day (n=21) to male CSQ TG mouse (6-week-old) as adilated cardiomyopathy model. As a normal control, non-Tg mouse (n=5) obtained from the same litter was used.

Results

Figure 10:
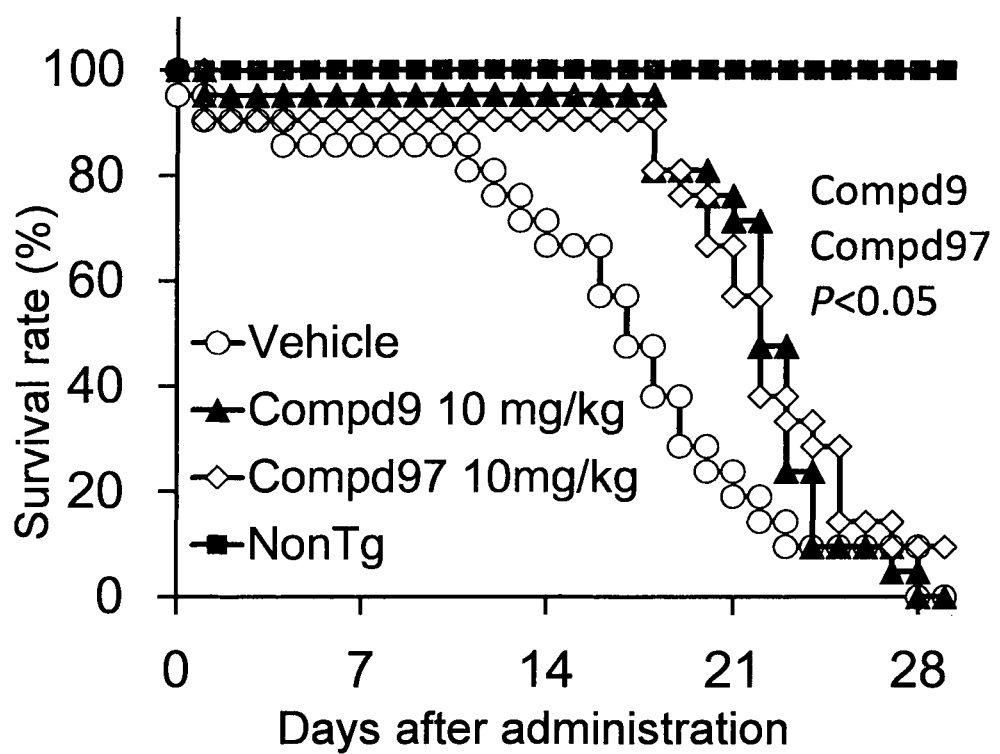
FIG. 10 shows the survival rate of male CSQ TG mouse after administration of compound 97 and compound 9.

The results are shown in FIG. 10. As the Kaplan-Meier survival curve shows, all compounds showed a significant life prolonging effect on the life of CSQ TG mouse.

Compd 9: compound 9, Compd 97: compound 97 n=21 (CSQ TG mouse), n=5 (non-TG mouse)

compound 9, log-rank $\chi^2$=5.7672*P<0.05;

compound 97, log-rank $\chi^2$=5.9304*P<0.05.

Formulation Example 1 (Production of Capsule)

| | |
|---|---|
| 1) compound of Example 1 | 30 mg |
| 2) fine powder cellulose | 10 mg |
| 3) lactose | 19 mg |
| 4) magnesium stearate | 1 mg |
| Total | 60 mg |

1), 2), 3) and 4) are mixed and filled in a gelatin capsule.

Formulation Example 2 (Production of Tablet)

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

INDUSTRIAL APPLICABILITY

The compound of the present invention has an IP6K inhibitory action and is expected to be useful as a prophylactic or therapeutic agent for diseases such as cardiac failure, diabetes and the like.

This application is based on patent application No. 2017-066579 filed in Japan (filing date: Mar. 30, 2017), the contents of which are encompassed in full herein.

The invention claimed is:
1. A compound represented by the formula:

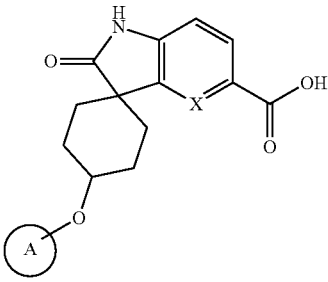

(I)

wherein
ring A is an optionally substituted aromatic ring;
X is CH or N
or a salt thereof.

2. The compound according to claim 1, wherein the ring A is a $C_{6-14}$ aromatic hydrocarbon ring or a 5- to 14-membered aromatic heterocycle, each of which is optionally substituted by 1 to 3 substituents selected from
(a) a halogen atom,
(b) a cyano group,
(c) a carbamoyl group,
(d) an optionally halogenated $C_{1-6}$ alkyl group,
(e) a $C_{1-6}$ alkoxy group,
(f) a $C_{3-10}$ cycloalkyl group, and
(g) a $C_{7-16}$ aralkyloxy group,
or a salt thereof.

3. 4-((3,5-Dichloropyridin-2-yl)oxy)-2'-oxo-1',2'-dihydrospiro[cyclohexane-1,3'-indole]-5'-carboxylic acid or a salt thereof.

4. 4-((3,5-dichloropyridin-2-yl)oxy)-2'-oxo-1',2'-dihydrospiro[cyclohexane-1,3'-pyrrolo[3,2-b]pyridine]-5'-carboxylic acid or a salt thereof.

5. 2'-oxo-4-(2,4,6-trichlorophenoxy)-1',2'-dihydrospiro[cyclohexane-1,3'-indole]-5'-carboxylic acid or a salt thereof.

6. 4-(2,4-dichlorophenoxy)-2'-oxo-1',2'-dihydrospiro[cyclohexane-1,3'-indole]-5'-carboxylic acid or a salt thereof.

7. 4-((3-chloro-5-(trifluoromethyl)pyridin-2-yl)oxy)-2'-oxo-1',2'-dihydrospiro[cyclohexane-1,3'-indole]-5'-carboxylic acid or a salt thereof.

8. 4-(4-chloro-2-methoxyphenoxy)-2'-oxo-1',2'-dihydrospiro[cyclohexane-1,3'-indole]-5'-carboxylic acid or a salt thereof.

9. 4-((5-chloro-3-fluoropyridin-2-yl)oxy)-2'-oxo-1',2'-dihydrospiro[cyclohexane-1,3'-indole]-5'-carboxylic acid or a salt thereof.

10. 4-(2,4-dichlorophenoxy)-2'-oxo-1',2'-dihydrospiro[cyclohexane-1,3'-pyrrolo[3,2-b]pyridine]-5'-carboxylic acid or a salt thereof.

11. 4-((3-chloro-5-(trifluoromethyl)pyridin-2-yl)oxy)-2'-oxo-1',2'-dihydrospiro[cyclohexane-1,3'-pyrrolo[3,2-b]pyridine]-5'-carboxylic acid or a salt thereof.

12. A composition comprising the compound according to claim 1 or a salt thereof, and a pharmacologically acceptable carrier.

13. A method for the treatment of a disease selected from cardiac failure and diabetes in a mammal, comprising administering an effective amount of the composition according to claim 12 to the mammal.

14. A method for inhibiting inositol hexakisphosphate kinase in a mammal, comprising administering an effective amount of the composition according to claim 12 to the mammal.

15. A method for the treatment of a disease selected from cardiac failure and diabetes in a mammal, comprising administering an effective amount of the compound according to claim 1 or a salt thereof to the mammal.

16. A method for inhibiting inositol hexakisphosphate kinase in a mammal, comprising administering an effective amount of the compound according to claim 1 or a salt thereof to the mammal.

17. 4-((3,5-difluoropyridin-2-yl)oxy)-2'-oxo-1',2'-dihydrospiro[cyclohexane-1,3'-indole]-5'-carboxylic acid or a salt thereof.

18. 4-(4-chloro-2-fluorophenoxy)-2'-oxo-1',2'-dihydrospiro[cyclohexane-1,3'-indole]-5'-carboxylic acid or a salt thereof.

* * * * *